United States Patent
Rands et al.

(10) Patent No.: US 11,471,417 B2
(45) Date of Patent: *Oct. 18, 2022

(54) DEUTERATED N,N-DIMETHYLTRYPTAMINE COMPOUNDS

(71) Applicant: Small Pharma Ltd, London (GB)

(72) Inventors: Peter Rands, London (GB); Tiffanie Benway, London (GB); Zelah Joel, London (GB); Marie Layzell, London (GB); Ellen James, London (GB)

(73) Assignee: Small Pharma Ltd, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/458,167

(22) Filed: Aug. 26, 2021

(65) Prior Publication Data

US 2021/0403426 A1 Dec. 30, 2021

Related U.S. Application Data

(63) Continuation of application No. PCT/EP2021/060750, filed on Apr. 23, 2021.

(30) Foreign Application Priority Data

| Jun. 2, 2020 | (GB) | 2008303 |
| Jun. 2, 2020 | (WO) | PCT/EP2020/065244 |
| Dec. 1, 2020 | (GB) | 2018950 |
| Dec. 1, 2020 | (GB) | 2018955 |
| Mar. 22, 2021 | (GB) | 2103981 |

(51) Int. Cl.
| *C07D 209/16* | (2006.01) |
| *A61K 9/48* | (2006.01) |
| *A61K 31/4045* | (2006.01) |
| *A61K 9/00* | (2006.01) |
| *A61K 9/50* | (2006.01) |
| *A61K 9/20* | (2006.01) |
| *C07B 59/00* | (2006.01) |

(52) U.S. Cl.
CPC ............ *A61K 9/485* (2013.01); *A61K 9/0053* (2013.01); *A61K 9/2009* (2013.01); *A61K 9/2013* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61K 9/5057* (2013.01); *A61K 31/4045* (2013.01); *C07B 59/002* (2013.01); *C07D 209/16* (2013.01); *C07B 2200/05* (2013.01)

(58) Field of Classification Search
CPC .................................................. C07D 209/16
See application file for complete search history.

(56) References Cited

U.S. PATENT DOCUMENTS

| 4,336,378 A | * | 6/1982 | Brand .................. C07D 261/08 544/137 |
| 8,268,856 B2 | | 9/2012 | Hamann et al. |
| 11,000,534 B1 | | 5/2021 | Sippy |

(Continued)

FOREIGN PATENT DOCUMENTS

| GB | 2585978 A | 1/2021 |
| GB | 2586940 A | 3/2021 |

(Continued)

OTHER PUBLICATIONS

Timmins, Expert Opin Ther Pat. Oct. 2014 ; 24(10): 1067-1075.*
Morris Philip E Jr et a.l, "Indolealkylamine Metabolism: Synthesis of Deuterated Indolealkylamines as Metabolic Probes", Journal of Labelled Compounds and Radiopharmaceuticals, John Wiley & Sons Ltd, vol. 33, No. 6, Jan. 11, 1993, 11 pages.
Barker et al., "Comparison of the brain levels of N N-Dimethyltryptamine and xxB B-Tetradeutero N, N-Dimethyltryptamine Following Intraperitoneal Injection", Biochemical Pharmacology, vol. 31, No. 15, Jan. 20, 1982, 4 pages.

(Continued)

*Primary Examiner* — Nizal S Chandrakumar
(74) *Attorney, Agent, or Firm* — Heslin Rothenberg Farley & Mesiti, P.C.

(57) ABSTRACT

Compounds, compositions, methods, and uses are described for therapeutic deuterated N,N-dimethyltryptamine compounds (e.g., a single compound or a plurality of deuterated N,N-dimethyltryptamine compounds) such as N,N-dimethyltryptamine compounds, α-protio, α-deutero-N,N-dimethyltryptamine compounds, α,α-dideutero-N,N-dimethyltryptamine compounds, and pharmaceutically acceptable salts of these compounds. The deuterated N,N-dimethyltryptamine compound may have an increased half-life compared with the half-life of undeuterated N,N-dimethyltryptamine. For example, a deuterated N,N-dimethyltryptamine compound may be used in therapy and have a Formula (I):

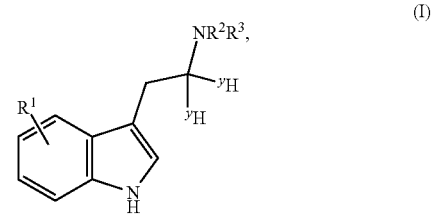

wherein:
the ratio of deuterium:protium in the compound is greater than that found naturally in hydrogen;
each $R^1$ is independently selected from H and D;
$R^2$ is selected from $CH_3$ and $CD_3$;
$R^3$ is selected from $CH_3$ and $CD_3$;
each $^yH$ is independently selected from H and D,
or a pharmaceutically acceptable salt thereof.

12 Claims, 4 Drawing Sheets

(56) References Cited

U.S. PATENT DOCUMENTS

| | | |
|---|---|---|
| 2002/0022667 A1 | 2/2002 | Pace et al. |
| 2009/0076121 A1 | 3/2009 | Czarnik |
| 2018/0221396 A1 | 8/2018 | Chadeayne |
| 2020/0339519 A1 | 10/2020 | Kim et al. |
| 2020/0390746 A1 | 12/2020 | Rands et al. |
| 2021/0378969 A1 | 12/2021 | Rands et al. |
| 2021/0395201 A1 | 12/2021 | Rands et al. |
| 2022/0062237 A1 | 3/2022 | Layzell et al. |
| 2022/0062238 A1 | 3/2022 | Layzell et al. |
| 2022/0081396 A1 | 3/2022 | Rands et al. |

FOREIGN PATENT DOCUMENTS

| | | |
|---|---|---|
| GB | 2596884 A | 1/2022 |
| WO | 02083144 A1 | 10/2002 |
| WO | 2004085392 A1 | 10/2004 |
| WO | 2008049116 A2 | 4/2008 |
| WO | 2008071455 A1 | 6/2008 |
| WO | 2009049030 A1 | 4/2009 |
| WO | 2018195455 A1 | 10/2018 |
| WO | WO 2019-081764 A1 | 5/2019 |
| WO | 2020169850 A1 | 8/2020 |
| WO | 2020169851 A1 | 8/2020 |
| WO | 2020176597 A1 | 9/2020 |
| WO | 2020176599 A1 | 9/2020 |
| WO | WO 2020-245133 A1 | 12/2020 |
| WO | WO 2021-089872 A1 | 5/2021 |
| WO | WO 2021-089873 A1 | 5/2021 |
| WO | 2021116503 A2 | 6/2021 |
| WO | 2021155470 A1 | 8/2021 |
| WO | 2021234608 A1 | 11/2021 |
| WO | 2022031566 A1 | 2/2022 |
| WO | 2022043227 A1 | 3/2022 |
| WO | 2022069690 A2 | 4/2022 |

OTHER PUBLICATIONS

Beaton et al., "A Comparison of the Behavioral Eeffects of Proteo- and Deurero-N, N-Dimethrltryptamine", Pharmacology, Biochemistry & Behavior, vol. 16, Sep. 8, 1982, 4 pages.

Dyck, et al. "Effects of Deuterium Substitution on the Disposition of Intraperitoneal Tryptamine", Biochemical pharmacology, 1986, 4 pages.

Barker, et al., N,N-Dimethyltryptamine (DMT), an Endogenous Hallucinogen: Past, Present, and Future Research to Determine Its Role and Function, Frontiers in Neuroscience, Aug. 2018, 17 pages.

Brandt, et al., "Microwave-Accelerated Synthesis of Psychoactive Deuterated N, N-Dialkylated-[a, a, ?, ?-d4]-Tryptamines", Journal of Labelled Compounds and Radiopharmaceuticals, vol. 51, No. 14, pp. 423-429 Nov. 1, 2008.

Walker, et al., "Gas Chromatographic-Mass Spectrometric Isotope Dilution Assay for N,N-Dimethyltryptamine in Human Plasma", Biochemical Medicine, vol. 8, pp. 105-113 1973.

Halberstadt et al., "Behavorial effects of $\alpha,\alpha,\beta\beta$-tetradeutero-5-MeO-DMT in rats: comparison with 5-MeO-DMT administered in combination with a monoamine oxidase inhibitor", Psychopharmacology, vol. 221, pp. 709-718 Jan. 6, 2012.

Tearavarich, et al., "Microwave-Accelerated Preparation and Analytical Characterization of 5-ethoxy-N,N-dialkyl-[$\alpha$, $\alpha$, 62 ,$\beta$-H4]- and [$\alpha,\alpha,\beta,\beta$-D4]-tryptamines", Drug Testing and Analysis, vol. 3, No. 9, pp. 597-608 Dec. 2010.

Celik, et al., "Binding of Serotonin to the Human Serotonin Transporter. Molecular Modeling and Experimental Validation" Journal of the American Chemical Society, vol. 130, No. 12, pp. 3853-3865 Mar. 2008.

Celik, et al., "Supplementary Information to Binding of Serotonin to the Human Serotonin Transporter. Molecular Modeling and Experimental Validation", Journal of the American Chemical Society, 14 pages Mar. 2008.

McIlhenny, et al., "Direct Analysis of Psychoactive Tryptamine and Harmala Alkaloids in the Amazonian Botanical Medicine Ayahuasca by Liquid Chromatography-electrospray Ionization-tandem Mass Spectrometry", Journal of Chromatography A, vol. 1216, No. 51, 9 p. 2009.

Queiroz, et al., "Chemical Composition of the Bark of Tetrapterys Mucronata and Identification of Acetylcholinesterase Inhibitory Constituents", Journal of Natural Products, vol. 77, No. 3, 2014, pp. 650-656 2014.

Servillo, et al., "Citrus Genus Plants Contain N-Methylated Tryptamine Derivatives and Their 5-Hydroxylated Forms", Journal of Agricultural and Food Chemistry, vol. 61, No. 21, pp. 5156-5162 2013.

Grina, et al., "Old and New Alkaloids From Zanthoxylum Arborescens", Journal of Organic Chemistry, vol. 47, No. 13, pp. 2648-2651 1982.

Ghosal, et al., "Indole Bases of Desmodium Gyrans", Phytochemistry (Elsevier), vol. 11, No. 5, pp. 1863-1864 1972.

Ambinter Screening Library, CAS Registry No. 1794811-18-9, Order No. Cat. Amb33838664 Mar. 26, 2020.

Aurora Building Blocks 2, CAS Registry No. 1435934-64-7, Order No. Cat A17.921.638. Feb. 27, 2020.

MuseChem Product List, CAS Registry No. 1794756-39-0, Order No. Cat. R055190. Apr. 21, 2020.

Dameron, et el., "Effects of N,N-Dimethyltryptamine on Rat Behaviors Relevant to Anxiety and Depression", ACS Chemical Neuroscience, vol. 9, No. 7, pp. 1582-1590 2018.

Sard, et al., "SAR of psilocybin analogs: Discovery of a selective 5-HT2c agonist", Bioorganic & Medicinal Chemistry Letters 15, vol. 15, No. 20, pp. 4555-4559 2005.

Ibrahim, et al., "Marine inspired 2-(5-Halo-1 H-indol-3-yl)-N,N-dimethylethanamines as Modulators of Serotonin Receptors: An Example lllusliating the Power of Bromine as Part of the Uniquely Marine Chemical Space", Marine drugs, vol. 15, No. (8), pp. 248/1-248/14 2017.

Riga, et al., The serotonin hallucinogen 5-MeO-DMT alters corticothalamic activity in freely moving mice: Regionally-selective involvement of 5-HT1A and 5-HT2A receptors, Neuropharmacology, vol. 142, pp. 219-230 2017.

Gaujac, et al., Investigations into the polymorphic properties of N,N-dimethyltryptamine by X-ray diffraction and differential scanning calorimetry, Microchemical Journal, vol. 110, pp. 146-157 pp. 2013.

Chemieliva Pharmaceutical Product, CAS Registry No. 1794811-18-9, "Supplementary Disclosures", Chemieliva Pharmaceutical Product List, Order No. Cat CC0034141 Jan. 28, 2021.

Chemieliva Pharmaceutical Product, CAS Registry No. 1794756-39-0, "Supplementary Disclosures", Chemieliva Pharmaceutical Product List, Order No. Cat CC0034145 Jan. 28, 2021.

Strassman et al., "Dose-Response Study of N, N-Dimethyltryptamine in Humans: II. Subjective Effects and Preliminary Results of a New Rating Scale", Archives of General Psychiatry, Chicago, IL, vol. 51(2), pp. 98-108 Feb. 1994.

Dunlap et al., "Identification of Psychoplastogenic N,N-Dimethylaminoisotryptamine (isoDMT) Analogues through Structure—Activity Relationship Studies", Journal of Medicinal Chemistry, vol. 63, pp. 1142-1155 2020.

Timmins, "Deuterated Drugs; Where Are We Now?" Expert Opin Ther Pat., 24(10), pp. 1067-1075. Oct. 2014.

Rands et al., Unpublished U.S. Appl. No. 17/616,345, filed Dec. 3, 2021.

Rands et al., Unpublished U.S. Appl. No. 17/469,063, filed Sep. 8, 2021.

Rands et al., Unpublished U.S. Appl. No. 17/574,424, filed Jan. 12, 2022.

Rands et al., Unpublished U.S. Appl. No. 17/680,411, filed Feb. 25, 2022.

Brito-da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.

* cited by examiner

DEUTERATED N,N-DIMETHYLTRYPTAMINE COMPOUNDS

CROSS-REFERENCE TO RELATED APPLICATIONS

This application is a continuation of Patent Cooperation Treaty Application No. PCT/EP2021/060750, filed Apr. 23, 2021, which claims priority from United Kingdom Application No. 2008303.6, filed Jun. 2, 2020, Patent Cooperation Treaty Application No. PCT/EP2020/065244, filed Jun. 2, 2020, United Kingdom Application No. 2018950.2, filed Dec. 1, 2020, and United Kingdom Application No. 2018955.1 filed Dec. 1, 2020, the entire disclosures of each of which are incorporated by reference herein.

BACKGROUND

Classical psychedelics have shown preclinical and clinical promise in treating psychiatric disorders (Carhart-Harris and Goodwin (2017), *The Therapeutic Potential of Psychedelic Drugs: Past, Present and Future*, Neuropsychopharmacology 42, 2105-2113). In particular, psilocybin has demonstrated significant improvement in a range of depression and anxiety rating scales in randomised double blind studies (Griffiths et al. (2016), *Psilocybin produces substantial and sustained decreases in depression and anxiety in patients with life-threatening cancer; a randomised double-blind trial*, Journal of Psychopharmacology 30(12), 1181-1197).

N,N-dimethyltryptamine (DMT) is also understood to hold therapeutic value as a short-acting psychedelic, however its duration of action (under 20 minutes) is so short as to limit effective therapy. Administration protocols have been developed to extend the immersive psychedelic experience of DMT (Gallimore and Strassman (2016), *A model for the application of target-controlled intravenous infusion for a prolonged immersive DMT psychedelic experience*, Frontiers in Pharmacology, 7:211). However, these protocols carry risk of toxic buildup in patients who are poor metabolisers of DMT (for further discussion see Strassman et al (1994), *Dose response study of N,N-dimethyltryptamine in humans*, Arch Gen Psychiatry 51, 85).

α,α,β,β-Tetradeutero-N,N-dimethyltryptamine is known to exhibit a kinetic isotope effect which bestows a significant difference on its in vivo pharmacokinetic profile as compared with N,N-dimethyltryptamine. Substitution of hydrogen with a deuterium at an spa carbon centre is known to give rise to a 'kinetic isotope effect' by virtue of the difference in bond strength between a CH and a CD bond. First demonstrated in 1982 (Barker et al. (1982), *Comparison of the brain levels of N,N-dimethyltryptamine and α,α,β,β-tetradeutero-N,N-dimethyltryptamine following intraperitoneal injection*, Biochemical Pharmacology, 31(15), 2513-2516), the half-life of α,α,ββ-tetradeutero-N,N-dimethyltryptamine in the rodent brain is suggestive that administration of α,α,ββ-tetradeutero-N,N-dimethyltryptamine alone would maintain a patient in DMT space for longer than therapeutically essential.

SUMMARY

Compounds, compositions, methods, and uses are disclosed for therapeutic deuterated N,N-dimethyltryptamine compounds (e.g., a single compound or a plurality of deuterated N,N-dimethyltryptamine compounds) such as N,N-dimethyltryptamine compounds, α-protio, α-deutero-N,N-dimethyltryptamine compounds, α,α-dideutero-N,N-dimethyltryptamine compounds, and pharmaceutically acceptable salts of these compounds. The deuterated N,N-dimethyltryptamine compound may have an increased half-life compared with the half-life of undeuterated N,N-dimethyltryptamine. The deuterated N,N-dimethyltryptamine compound may have a Formula (I):

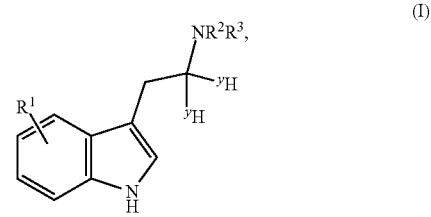

wherein:
the ratio of deuterium:protium in the compound is greater than that found naturally in hydrogen;
each $R^1$ is independently selected from H and D;
$R^2$ is selected from $CH_3$ and $CD_3$;
$R^3$ is selected from $CH_3$ and $CD_3$;
each $^yH$ is independently selected from H and D,
or a pharmaceutically acceptable salt thereof.

Further aspects and embodiments will be evident from the discussion that follows below.

DETAILED DESCRIPTION

Figure 1:
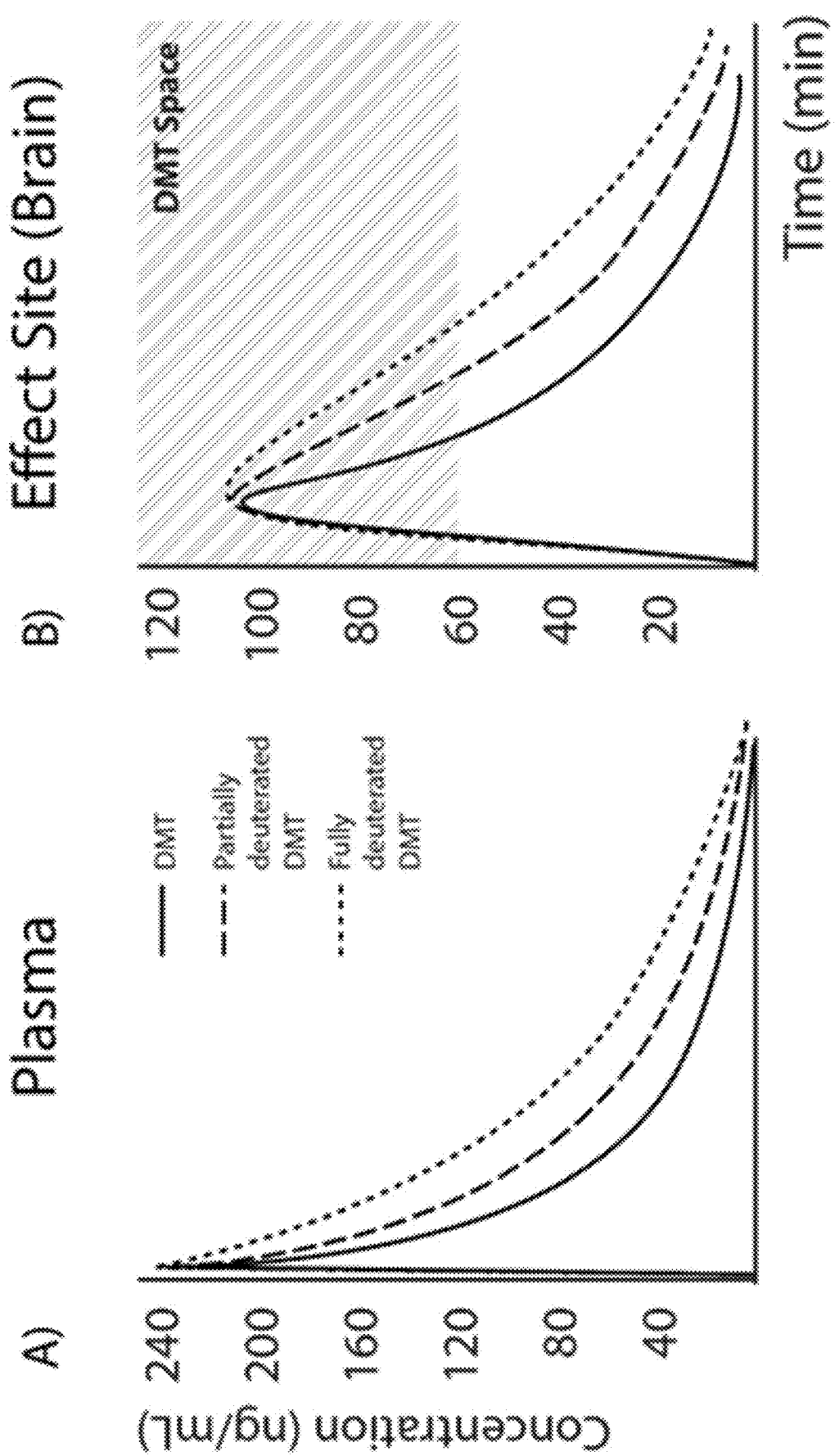
FIG. 1. depicts the predicted pharmacokinetic profile of partially deuterated DMT compared to undeuterated DMT and fully deuterated DMT. Predicted A) plasma concentration and B) brain tissue concentration, showing the extended half-life of partially deuterated DMT. Hashed area depicts effect site concentrations (>60 ng/mL) that are experienced as full dissociation from the external world, referred to as 'DMT space'.

Throughout this specification, one or more aspect may be combined with one or more other aspects or features described in the specification to define distinct embodiments.

References herein to a singular of a noun encompass the plural of the noun, and vice-versa, unless the context implies otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention is based, in part, upon the ability to apply knowledge of the kinetic isotope effect exhibited by α,α,β,β-tetradeutero-N,N-dimethyltryptamine in order to modify, controllably, the pharmacokinetic profile of N,N-dimethyltryptamine, thereby permitting more flexible therapeutic application. In particular, by providing individual drug substance compositions comprising deuterated N,N-dimethyltryptamine analogues, in particular N,N-dimethyltryptamine comprising at least one deuterium atom at the alpha position (e.g., attached to the carbon atom to which the dimethylamino moiety is attached), described are compositions and methods which enable a finely tuned single dose to maintain a patient in full dissociation from the external world, referred to herein as 'DMT space', for a therapeutically optimised duration without relying on infusion protocols or combination therapy with monoamine oxidase inhibitors in the clinic. A clinically applicable solution which reduces clinical complexity and increases clinical flexibility in the administration of DMT-assisted therapy is provided.

Moreover, we have observed a quantifiable relationship between the extent of deuteration, and by proxy the H:D ratio of input reducing agent in synthetic methods disclosed herein, and the effect on potentiation (e.g., increase) of the metabolic half-life of the parent compound. Such technical effect may be used to quantifiably increase the precision with which deuterated N,N-dimethyltryptamine compositions (that is to say isolated deuterium-containing N,N-dimethyltryptamine compounds or compositions comprising more than one type of compound selected from N,N-dimethyltryptamine and its deuterated analogues, in particular those deuterated at the alpha positions and/or N,N-dimethyl positions, or pharmaceutically acceptable salts of these) may be prepared.

In a first aspect, deuterated N,N-dimethyltryptamine compounds (e.g., a single compound or a plurality of deuterated N,N-dimethyltryptamine compounds) such as N,N-dimethyltryptamine compounds, α-protio, α-deutero-N,N-dimethyltryptamine compounds, α,α-dideutero-N,N-dimethyltryptamine compounds, and pharmaceutically acceptable salts of these compounds, preferably wherein the deuterated N,N-dimethyltryptamine compound has an increased half-life compared with the half-life of undeuterated N,N-dimethyltryptamine are used for therapy.

In a second aspect, a deuterated N,N-dimethyltryptamine compound of Formula (I) for use in therapy is provided:

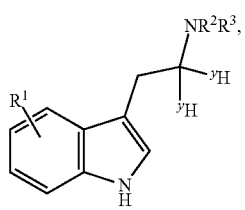

(I)

wherein, the ratio of deuterium:protium in the compound is greater than that found naturally in hydrogen:
each $R^1$ is independently selected from H and D;
$R^2$ is selected from $CH_3$ and $CD_3$;
$R^3$ is selected from $CH_3$ and $CD_3$;
ach $^yH$ is independently selected from H and D,
or a pharmaceutically acceptable salt thereof.

In preferred embodiments of the second aspect, each $R^1$ is H. In primary embodiments of the second aspect both $^yH$ are D. In secondary embodiments of the second aspect both $R^2$ and $R^3$ are $CD_3$.

Viewed from a third aspect, a compound of Formula (I) or a pharmaceutically acceptable salt thereof, obtainable by a method of synthesis comprising reacting a compound of Formula (II) with $LiAlH_4$ and/or $LiAlD_4$, is provided:

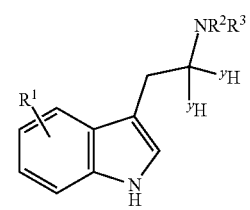

(I)

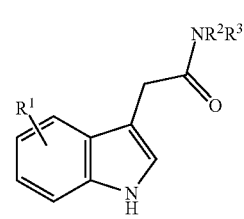

(II)

wherein $R^1$ is selected from H and D,
$R^2$ is selected from $CH_3$ and $CD_3$;
$R^3$ is selected from $CH_3$ and $CD_3$;
and each $^yH$ is independently selected from H and D.

Viewed from a fourth aspect, a pharmaceutical composition comprising a compound or composition as defined according to any one of the first to third aspects in combination with a pharmaceutically acceptable excipient is provided.

Viewed from a fifth aspect, a compound or composition as defined according to any one of the first to fourth aspects for use in a method of psychedelic-assisted psychotherapy is provided.

Viewed from a sixth aspect, a compound or composition as defined according to any one of the first to fifth aspects for use in a method of treating a neurological disorder or a psychological disorder in a patient is provided.

Viewed from a seventh aspect, a method of treating a neurological disorder or a psychological disorder comprising administering to a patient in need thereof a compound or composition as defined according to any one of the first to fourth aspects is provided.

Viewed from a eighth aspect, the use of a compound or composition as defined according to any one of the first to fourth aspects in the manufacture of a medicament for use in a method of treating a neurological disorder or a psychological disorder in a patient is provided.

Viewed from a ninth aspect, a method of preparing a compound in accordance with any of the first to third aspects comprising contacting deuterated or undeuterated 2-(3-indolyl)-N,N-dimethylacetamide with a reducing agent consisting essentially of lithium aluminium hydride and/or lithium aluminium deuteride is provided.

Viewed from a tenth aspect, a compound selected from Compounds 1-5, or a pharmaceutically acceptable salt thereof is provided.

1
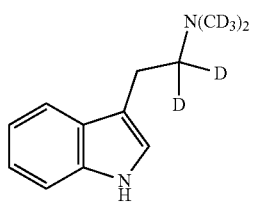

2
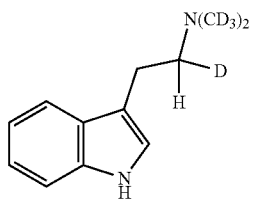

3
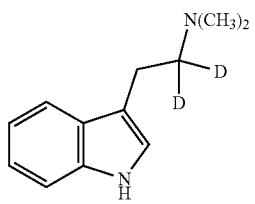

4
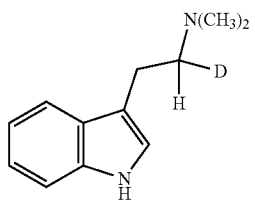

5
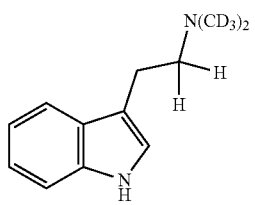

A deuterated N,N-dimethyltryptamine compound selected from N,N-dimethyltryptamine compounds, α-protio, α-deutero-N,N-dimethyltryptamine compounds α,α-dideutero-N,N-dimethyltryptamine compounds, and pharmaceutically acceptable salts of these compounds is provided.

As used herein, the term deuterated N,N-dimethyltryptamine compound means an N,N-dimethyltryptamine compound having a deuterium composition greater than found naturally occurring in hydrogen (approx. 1.6%). As used herein the term undeuterated N,N-dimethyltryptamine compound means an N,N-dimethyltryptamine compound having a deuterium composition equal to or less than found naturally occurring in hydrogen.

A protium atom (H) is a hydrogen atom with zero neutrons. A deuterium atom (D) is a hydrogen atom with one neutron. With reference to Formula Ia-Ic:

Ia
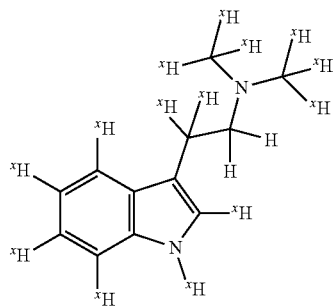

Ib
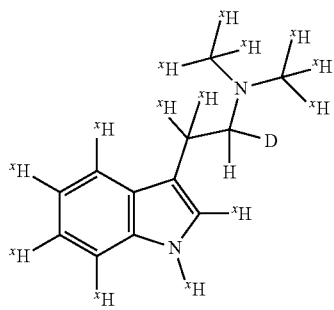

Ic
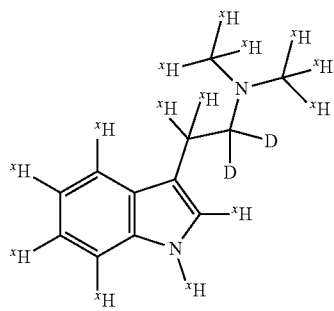

As used herein, the term N,N-dimethyltryptamine compounds means a compound of Formula Ia wherein each $^xH$ is independently selected from protium (H) and deuterium (D). For example, N,N-dimethyltryptamine compounds may comprise 0, 1 or 2 deuterium atoms at the β position. For the avoidance of doubt, the invention does not encompass a compound of Formula Ia where each $^xH$ is H.

As used herein, the term α-protio, α-deutero-N,N-dimethyltryptamine compounds means a compound of Formula Ib wherein each $^xH$ is independently selected from protium (H) and deuterium (D). For example, α-protio, α-deutero-N,N-dimethyltryptamine compounds may comprise 0, 1 or 2 deuterium atoms at the β position.

As used herein, the term α,α-dideutero-N,N-dimethyltryptamine compounds means a compound of Formula Ic wherein each $^xH$ is independently selected from protium (H) and deuterium (D). For example, α,α-dideutero-N,N-dimethyltryptamine compounds may comprise 0, 1 or 2 deuterium atoms at the β position.

The inventors have discovered that compounds exhibit a primary kinetic isotope effect when one or two deuterium atoms are positioned on the alpha carbon of an N,N-dimethyltryptamine compound. This primary kinetic isotope effect is exhibited to its fullest extent by α,α-dideutero-N,N-dimethyltryptamine compounds and to a lesser extent by α-protio, α-deutero-N,N-dimethyltryptamine compounds, such that the fold-change in half-life of an α-protio, α-deutero-N,N-dimethyltryptamine compound compared with the analogous N,N-dimethyltryptamine compound is about half that of the analogous α,α-dideutero-N,N-dimethyltryptamine compound.

Compositions comprising mixtures of two or more compounds selected from N,N-dimethyltryptamine, α,α-dideutero-N,N-dimethyltryptamine compounds and α-protio, α-deutero-N,N-dimethyltryptamine compounds can be used to apply the therapeutic benefits of the primary kinetic isotope effect to a variable degree.

Accordingly, a composition comprising two or more compounds selected from N,N-dimethyltryptamine compounds, α,α-dideutero-N,N-dimethyltryptamine compounds and α-protio, α-deutero-N,N-dimethyltryptamine compounds is provided.

The inventors have also discovered that compounds exhibit a secondary kinetic isotope effect when the N,N-dimethyl groups are deuterated. When such N,N-dimethyl groups comprise one or more deuterium and the alpha position is also mono- or di-deuterated, the secondary kinetic isotope is synergistic with the primary kinetic isotope effect, producing greater than a 14-fold increase in half-life compared with undeuterated N,N-dimethyltryptamine (see Example 3).

N,N-dimethyltryptamine and all its deuterated analogues freely form addition salts with anionic counterions. Throughout the specification, an N,N-dimethyltryptamine compound (in particular N,N-dimethyltryptamine, α,α-dideutero-N,N-dimethyltryptamine compounds and α-protio, α-deutero-N,N-dimethyltryptamine compounds) refers equally to any pharmaceutically acceptable salt, e.g., the fumarate salt.

Typically, acidic reagents may be used to prepare salts, in particular pharmaceutically acceptable salts, of N,N-dimethyltryptamine compounds. Examples of suitable acidic reagents are selected from the group consisting of fumaric acid, hydrochloric acid, tartaric acid, citric acid, hydrobromic acid, sulfuric acid, phosphoric acid, acetic acid, maleic acid, lactic acid, tartaric acid and gluconic acid. Often, where in the form of salts, N,N-dimethyltryptamine compounds, are fumarate, hydrochloride, tartrate or citrate salts, in particular fumarate salts.

The compounds of the first aspect, and indeed those of the second and third (and other, as appropriate) aspects, may thus be present in free base or salt form (such as the salts described herein), optionally as solvates (e.g., hydrates) thereof.

Embodiments of the first aspect provide a composition comprising 2% or more by weight of one or more deuterated N,N-dimethyltryptamine compound. In preferred embodiments of the first aspect, the composition comprises 5% or more by weight of the one or more deuterated N,N-dimethyltryptamine compound. In preferred embodiments of the first aspect, the composition comprises 10% or more by weight of the one or more deuterated N,N-dimethyltryptamine compound. In preferred embodiments of the first aspect, the composition comprises 15% or more by weight of the one or more deuterated N,N-dimethyltryptamine compound. In preferred embodiments of the first aspect, the composition comprises 20% or more by weight of the one or more deuterated N,N-dimethyltryptamine compound. In preferred embodiments of the first aspect, the composition comprises 25% or more by weight of the one or more deuterated N,N-dimethyltryptamine compound. In preferred embodiments of the first aspect, the composition comprises 30% or more by weight of the one or more deuterated N,N-dimethyltryptamine compound. In preferred embodiments of the first aspect, the composition comprises 50% or more by weight of the one or more deuterated N,N-dimethyltryptamine compound. In preferred embodiments of the first aspect, the composition comprises 60% or more by weight of the one or more deuterated N,N-dimethyltryptamine compound. In preferred embodiments of the first aspect, the composition comprises 75% or more by weight of the one or more deuterated N,N-dimethyltryptamine compound. In preferred embodiments of the first aspect, the composition comprises up to 90% by weight of the one or more deuterated N,N-dimethyltryptamine compounds. In preferred embodiments of the first aspect, the composition comprises up to 95% by weight of the one or more deuterated N,N-dimethyltryptamine compound. In preferred embodiments of the first aspect, the composition comprises up to 96% by weight of the one or more deuterated N,N-dimethyltryptamine compound. In preferred embodiments of the first aspect, the composition comprises up to 97% by weight of the one or more deuterated N,N-dimethyltryptamine compound. In preferred embodiments of the first aspect, the composition comprises up to 98% by weight of the one or more deuterated N,N-dimethyltryptamine compound. In preferred embodiments of the first aspect, the composition comprises up to 99% by weight of the one or more deuterated N,N-dimethyltryptamine compound. In preferred embodiments of the first aspect, the composition comprises up to 99.5% by weight of the one or more deuterated N,N-dimethyltryptamine compound. In preferred embodiments of the first aspect, the composition comprises up to 99.9% by weight of the one or more deuterated N,N-dimethyltryptamine compound.

Accordingly, it will be understood from the foregoing that, according to particular embodiments of the first aspect, in particular those embodiments discussed in the following eight paragraphs, the composition comprises between 2% and 90%, 2% and 95%, 2% and 96%, 2% and 97%, 2% and 98%, for example between 5% and 90%, 5% and 95%, 5% and 96%, 5% and 97%, 5% and 98%; 10% and 90%, 10% and 95%, 10% and 96%, 10% and 97%, 10% and 98%; 15% and 90%, 15% and 95%, 15% and 96%, 15% and 97%, 15% and 98%; 20% and 90%, 20% and 95%, 20% and 96%, 20% and 97%, 20% and 98%; 25% and 90%, 25% and 95%, 25% and 96%, 25% and 97%, 25% and 98%; 30% and 90%, 30% and 95%, 30% and 96%, 30% and 97%, 30% and 98%; 50% and 90%, 50% and 95%, 50% and 96%, 50% and 97%, 50% and 98%; 60% and 90%, 60% and 95%, 60% and 96%, 60% and 97%, 60% and 98%; or 75% and 90%, 75% and 95%, 75% and 96%, 75% and 97%, 75% and 98%, 75% and 99%, 90% and 99%, 90% and 99.9%, 99% and 99.9%, by weight of one or more deuterated N,N-dimethyltryptamine compound.

It will be understood that, wherever a composition comprises 2% or more by weight of one or more deuterated N,N-dimethyltryptamine compounds, that such compositions may comprise up to 95% by weight of one or more deuterated N,N-dimethyltryptamine compounds, or up to 96% by weight, up to 97% by weight or up to 98% by weight.

In preferred embodiments, the one or more partially deuterated N,N-dimethyltryptamine compound comprises up to 50% by weight of the total composition.

According to other preferred embodiments of the first aspect, the composition comprises up to 50% by weight, based on the total weight of the composition, of one or more compounds selected from α,α-dideutero-N,N-dimethyltryptamine compounds, α-protio, α-deutero-N,N-dimethyltryptamine compounds and pharmaceutically acceptable salts thereof. It will be understood that, in such embodiments, such compositions may comprise 2% or more by weight, for example 5% or more, 10% more, 15% more, 20% or more, 25% or more or 30% or more, based on the total composition, of the said one or more compounds.

According to specific embodiments, compositions, including all of the embodiments described herein, including but not limited to those embodiments comprising N,N-dimethyltryptamine, consist essentially of one or more compounds selected from N,N-dimethyltryptamine and its deuterated analogues, in particular those deuterated at the alpha position, or pharmaceutically acceptable salts of these. By the composition consisting essentially of one or more compounds selected from N,N-dimethyltryptamine and its deuterated analogues is meant that the composition may comprise additional components (other than N,N-dimethyltryptamine compounds) but that the presence of these additional components will not materially affect the essential characteristics of the composition. In particular, compositions consisting essentially of N,N-dimethyltryptamine compounds will not comprise material amounts of other pharmaceutically active substances (e.g., material amounts of other drug substances).

The composition may comprise from 2% to 98% by weight of N,N-dimethyltryptamine, and preferably comprises from 5% to 95% by weight of N,N-dimethyltryptamine. Preferred compositions comprise from 10% to 90% by weight of N,N-dimethyltryptamine, or from 15% to 85% by weight of N,N-dimethyltryptamine, or from 20% to 80% by weight of N,N-dimethyltryptamine, or from 25% to 75% by weight of N,N-dimethyltryptamine, or from 30% to 70% by weight of N,N-dimethyltryptamine, or from 40% to 60% by weight of N,N-dimethyltryptamine.

The composition preferably comprises from 5% to 99.9% by weight of a deuterated N,N-dimethyltryptamine compound selected from α,α-dideutero-N,N-dimethyltryptamine and α,α,β,β-tetradeutero-N,N-dimethyltryptamine.

A composition obtainable by the reduction of a composition obtainable by the reduction of 2-(3-indolyl)-N,N-dimethylacetamide with a reducing agent consisting essentially of lithium aluminium hydride and/or lithium aluminium deuteride is provided. In both aspects, the reducing agent may be dissolved or suspended in a liquid medium. Typically, owing to strong reactivity with water and protect solvents such as alcohols, although available in solid (powdered) form, lithium aluminium hydride (or deuteride) are often manipulated in dried, aprotic solvents such as ethers, often under an inert atmosphere. The skilled person is well aware of such precautions and appropriate protocols.

It will be understood that the disclosure provides a composition obtainable by the reduction of a composition comprising 2-(3-indolyl)-N,N-dimethylacetamide with a reducing agent consisting essentially of lithium aluminium hydride and/or lithium aluminium deuteride, optionally dissolved or suspended in a liquid medium. And, also provides a composition obtained by such reduction or, more generally, obtained by a reduction in accordance with the second or third aspect.

It is also to be understood that the amounts of N,N-dimethyltryptamine compounds described herein with specific reference to the composition of the first aspect may be applied mutatis mutandis to the compositions of the second and third aspects.

According to particular embodiments, by reciting that the reducing agent consists essentially of lithium aluminium hydride and/or lithium aluminium deuteride is meant that the reducing agent may comprise additional components but that the presence of these components will not materially affect the essential characteristics of the reducing agent (in particular stability and reductive propensity).

According to the fourth aspect, there is provided a pharmaceutical composition comprising a composition as defined in accordance with the first to third aspects, in combination with a pharmaceutically acceptable excipient.

The pharmaceutical composition comprises a composition (according to any one of its first to third aspects) in combination with one or more pharmaceutically acceptable excipients. Suitable pharmaceutical compositions can be prepared by the skilled person, with examples of pharmaceutically acceptable excipients including but not being limited to those described in Gennaro et. al., Remmington: *The Science and Practice of Pharmacy*, 20$^{th}$ Edition, Lippincott, Williams and Wilkins, 2000 (specifically part 5: pharmaceutical manufacturing). Suitable excipients are also described in the Handbook of Pharmaceutical Excipients, 2$^{nd}$ Edition; Editors A. Wade and P. J. Weller, American Pharmaceutical Association, Washington, The Pharmaceutical Press, London, 1994.

Described pharmaceutical compositions are expected to display superior oral bioavailability compared with undeuterated N,N-dimethyltryptamine. Accordingly, a compound or composition described herein may be compressed or otherwise formulated into solid dosage units, such as tablets, capsule, orally disintegrating tablets, thin films, buccal patches and buccal tablets, or be processed into capsules or suppositories. When formulated as an orally disintegrating tablet, a compound or composition described is compatible with the Zydis® platform. A Zydis® tablet is produced by lyophilizing or freeze-drying a freebase compound or composition in a matrix. The resulting product is very lightweight. Such embodiments of a formulation comprise particles, preferably with a particle size of less than 50 mm, of a compound or composition physically suspended in a water-soluble matrix which is then lyophilized. An orally disintegrating tablet formulated this way dissolves rapidly when placed in mouth.

By means of pharmaceutically suitable liquids the compounds can also be prepared in the form of a solution, suspension, emulsion, or as a spray. For making dosage units, including tablets, the use of conventional additives such as fillers, colorants, polymeric binders and the like is contemplated. In general, any pharmaceutically acceptable additive can be used.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

For parenteral administration, aqueous solutions, isotonic saline solutions and sterile injectable solutions may be used, containing pharmaceutically acceptable dispersing agents and/or wetting agents, such as propylene glycol or butylene glycol. Formulations suitable for inhalation, transdermal, mucosal or transmembrane administration comprise a freebase of a deuterated N,N-dimethyltryptamine compound, typically with one or more biocompatible excipient. Such formulations achieve a longer lasting therapeutic effect than equivalent formulations of undeuterated N,N-dimethyltryptamine.

Thus, an aspect provides a parenteral formulation comprising a freebase of one or more deuterated N,N-dimethyltryptamine compound selected from N,N-dimethyltryptamine compounds, α,α-dideutero-N,N-dimethyltryptamine compounds, α-protio, α-deutero-N,N-dimethyltryptamine compounds, together with a biocompatible excipient. In preferred embodiments the deuterated N,N-dimethyltryptamine compound is a compound of Formula I, wherein the ratio of deuterium:protium in the compound is greater than that found naturally in hydrogen; each $R^1$ is independently selected from H and D; $R^2$ is selected from $CH_3$ and $CD_3$; $R^3$ is selected from $CH_3$ and $CD_3$; and each $^3H$ is independently selected from H and D.

Typically the biocompatible excipient comprises a solvent. Preferably the solvent is selected from any one or a combination of two or more of propylene glycol, glycerine, polyethylene glycol, water, ethanol and triacetin. For preferred inhalable formulations the solvent is selected from propylene glycol, glycerine and polyethylene glycol, or a mixture thereof. Preferably the solvent is a mixture of propylene glycol and glycerine in a ratio of from about 50:50 to about 30:70 by weight. The concentration of the freebase is from about 1 mg/mL to about 1000 mg/mL. Preferably the biocompatible excipient comprises a taste-masking agent.

In preferred embodiments the formulation has an oxygen content of less than 2 ppm. In embodiments the formulation is stored in a container adapted to prevent penetration of ultraviolet light.

A pharmaceutical composition, in combination with packaging material suitable for the composition, the packaging material including instructions for the use of the pharmaceutical composition is contemplated.

The compositions are useful in therapy and may be administered to a patient in need thereof. As used herein, the term 'patient' preferably refers to a human patient, but may also refer to a domestic mammal. The term does not encompass laboratory mammals.

In accordance with the sixth aspect, there is provided a composition as defined according to any one of the first to fourth aspects for use in a method of treating a psychiatric disorder or a neurological disorder in a patient. The seventh aspect provides a method of treating a psychiatric disorder or a neurological disorder comprising administering to a patient in need thereof a composition as defined according to any one of the first to fourth aspects and the eighth aspect provides the use of a composition as defined according to any one of the first to fourth aspects in the manufacture of a medicament for use in a method of treating a psychiatric disorder or a neurological disorder in a patient. In embodiments of the sixth to eight aspects the psychiatric or neurological disorder is selected from (i) an obsessive compulsive disorder, (ii) a depressive disorder, (iii) a schizophrenia disorder, (iv) a schizotypal disorder, (v) an anxiety disorder, (vi) substance abuse, (vii) an avolition disorder, and (viii) a brain injury disorder.

As used herein the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom.

As used herein the term 'neurological disorder' means a disease of the central and peripheral nervous system.

Diagnostic criteria for psychiatric and neurological disorders referred to herein are provided in, for example, the Diagnostic and Statistical Manual of Mental Disorders, Fifth Edition, (DSM-5), the contents of which are incorporated herein by reference.

As used herein the term 'obsessive-compulsive disorder' is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically obsessive-compulsive disorder (OCD) manifests as one or more obsession which drives adoption of a compulsion. For example, an obsession with germs may drive a compulsion to clean. A compulsion can either be overt and observable by others, such as checking that a door is locked, or a covert mental act that cannot be observed, such as repeating a certain phrase in one's mind.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:
  depressed mood, such as feeling sad, empty or tearful (in children and teens, depressed mood can appear as constant irritability);
  significantly reduced interest or feeling no pleasure in all or most activities;
  significant weight loss when not dieting, weight gain, or decrease or increase in appetite (in children, failure to gain weight as expected);
  insomnia or increased desire to sleep;
  either restlessness or slowed behaviour that can be observed by others;
  fatigue or loss of energy;
  feelings of worthlessness, or excessive or inappropriate guilt;
  trouble making decisions, or trouble thinking or concentrating;
  recurrent thoughts of death or suicide, or a suicide attempt.

At least one of the symptoms must be either a depressed mood or a loss of interest or pleasure.

Persistent depressive disorder, also known as dysthymia, is defined as a patient exhibiting the following two features:
  A. has depressed mood for most the time almost every day for at least two years. Children and adolescents may have irritable mood, and the time frame is at least one year.
  B. While depressed, a person experiences at least two of the following symptoms:
    Either overeating or lack of appetite.
    Sleeping too much or having difficulty sleeping.
    Fatigue, lack of energy.
    Poor self-esteem.
    Difficulty with concentration or decision making.

As used herein the term 'treatment resistant depression' describes MDD which fails to achieve an adequate response to an adequate treatment with standard of care therapy.

As used herein 'bipolar disorder' also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely "up," elated, and energised behaviour (known as manic episodes, and defined further below) to very sad, "down," or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein the term 'substance abuse' means a patterned use of a drug in which the user consumes the substance in amounts or with methods which are harmful to themselves or others.

As used herein the term 'an avolition disorder' refers to a disorder which includes as a symptom the decrease in motivation to initiate and perform self-directed purposeful activities.

As used herein the term 'brain injury disorder' refers to an injury to the brain that occurs after birth and is not congenital, degenerative or hereditary. The term encompasses traumatic brain injury, for example from a car accident or a sports injury, and acquired brain injury, such as ischaemic stroke, transient ischaemic stroke, haemorrhagic stroke, brain tumour, meningitis or encephalitis, In preferred embodiments of the sixth to eighth aspects, the psychiatric or neurological disorder is selected from (i) an obsessive compulsive disorder, (ii) a depressive disorder, (iii) an anxiety disorder, (iv) substance abuse, (v) an avolition disorder, and (vi) a brain injury disorder.

According to particular embodiments of the sixth to eighth aspects, the depressive disorder is major depressive disorder. According to still more particular embodiments, the major depressive disorder is treatment-resistant major depressive disorder.

Compositions comprising deuterated N,N-dimethyltryptamine compounds can be synthesized at gram scale up to multi-kg scale following the reaction scheme (synthetic scheme) provided in Scheme 1.

The relative proportions of N,N-dimethyltryptamine compounds against deuterated N,N-dimethyltryptamine compounds and partially deuterated N,N-dimethyltryptamine compounds may be controlled by varying the ratio of lithium aluminium hydride and lithium aluminium deuteride in the reducing agent. Relative proportions may further be varied by adding one or more of N,N-dimethyltryptamine, $\alpha,\alpha$-dideutero-N,N-dimethyltryptamine and $\alpha,\alpha,\beta,\beta$-tetradeutero-N,N-dimethyltryptamine to the compositions described hereinabove.

A particular advantage of some embodiments of the present invention, in particular but not limited to the compositions obtainable in accordance with its third aspect and the method of its ninth aspect, is that the reductions described in accordance with these aspects allow particularly high purities to be obtained, without the necessity for subsequent chromatographic purification (e.g., column chromatography), thereby increasing the efficiency through which compositions may be prepared. Moreover, the ability to avoid the use of chromatography in order to achieve high purities makes scale up more efficient and therefore cost-effective.

Identification of the compositions obtained by methods may be achieved, if desired, by chromatographic separation of the components of the mixtures by conventional means at the disposal of the skilled person in combination with spectroscopic and/or mass spectrometric analysis.

Alternative compositions are obtainable by mixing undeuterated N,N-dimethyltryptamine, obtainable by Scheme 1 when the reducing agent is exclusively lithium aluminium hydride, with a deuterated N,N-dimethyltryptamine compound obtainable from Scheme 1 when the reducing agent is exclusively lithium aluminium deuteride.

The compositions described hereinabove may be further modified by adding one or more deuterated N,N-dimethyltryptamine compounds. Stocks of such deuterated N,N-dimethyltryptamine compounds may be obtained, for example, from the chromatographic separation described above. In this way, for example, the compounds of the tenth aspect may be obtained.

Whilst identification of the compositions resultant from the reduction described herein may be achieved by chromatographic separation of the components of the mixtures, in combination with spectroscopic and/or mass spectrometric analysis, a particular benefit is that, according to particular embodiments, there may be no necessity to do so. This is because, over and above the purities achievable, we have as alluded to above recognized that there is a quantifiable relationship between the extent of deuteration (or in other words the quantity or proportion of deuterium in the N,N-dimethyltryptamine compounds in the compositions) and the metabolic half-life of the resultant composition. The extent of deuteration may be controlled through the amount of deuterium-containing reducing agent used in the methods, through which (according to particular embodiments) the compositions may be obtained, and thus control exercised, in a predictable way, over potentiation of the metabolic half-life of the parent compound (undeuterated N,N-dimethyltryptamine).

Figure 2:
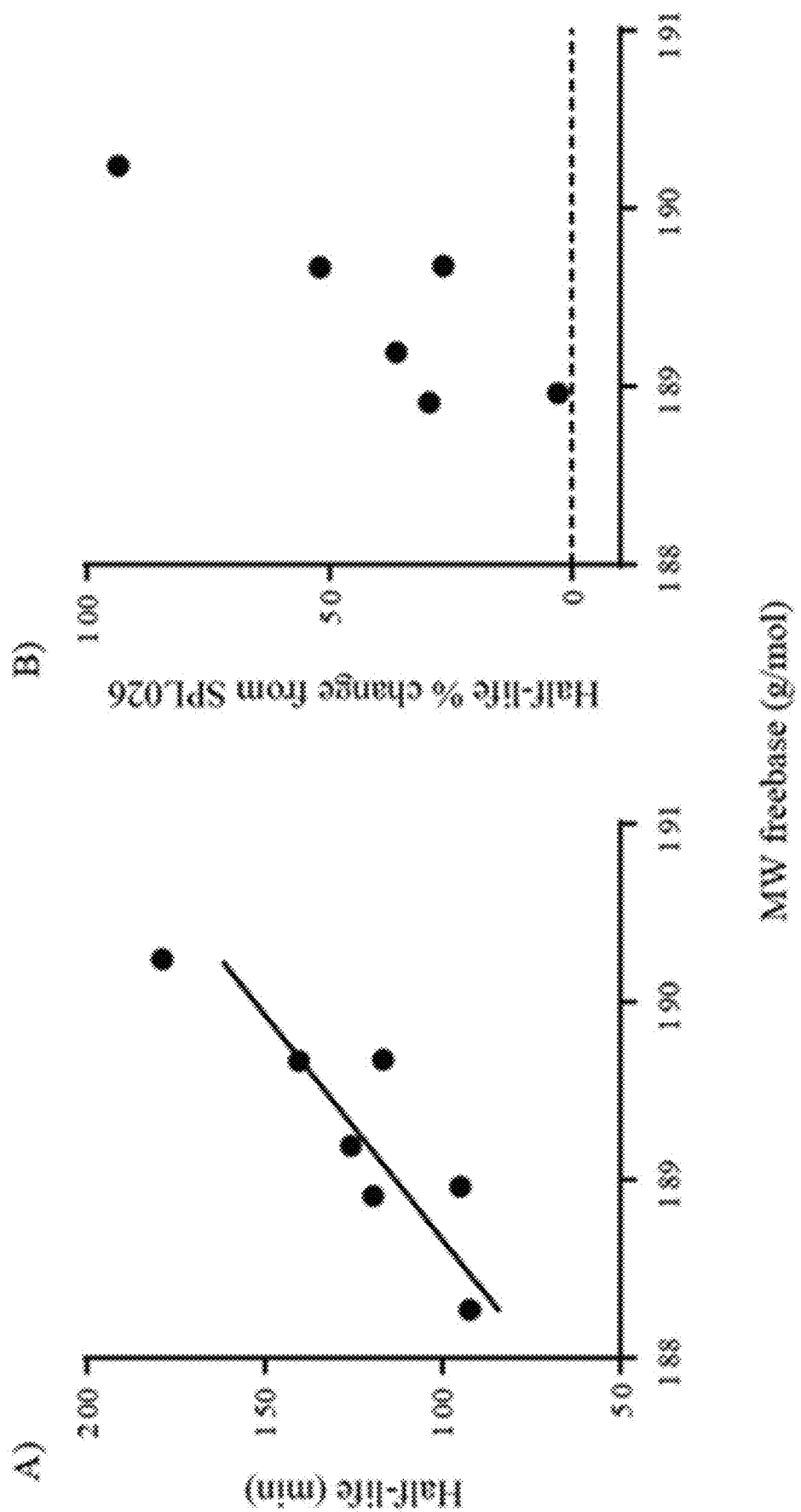
FIG. 2 plots calculated in vitro half-life for DMT and 6 deuterated-containing compositions described in Example 1. A) Linear regression analysis. The r2 value for half-life is 0.754; where the slope was found to be significantly different to zero, p=0.01. B) Half-life of deuterated analogues as a percent change from (undeuterated) DMT (dashed line).
Figure 3:
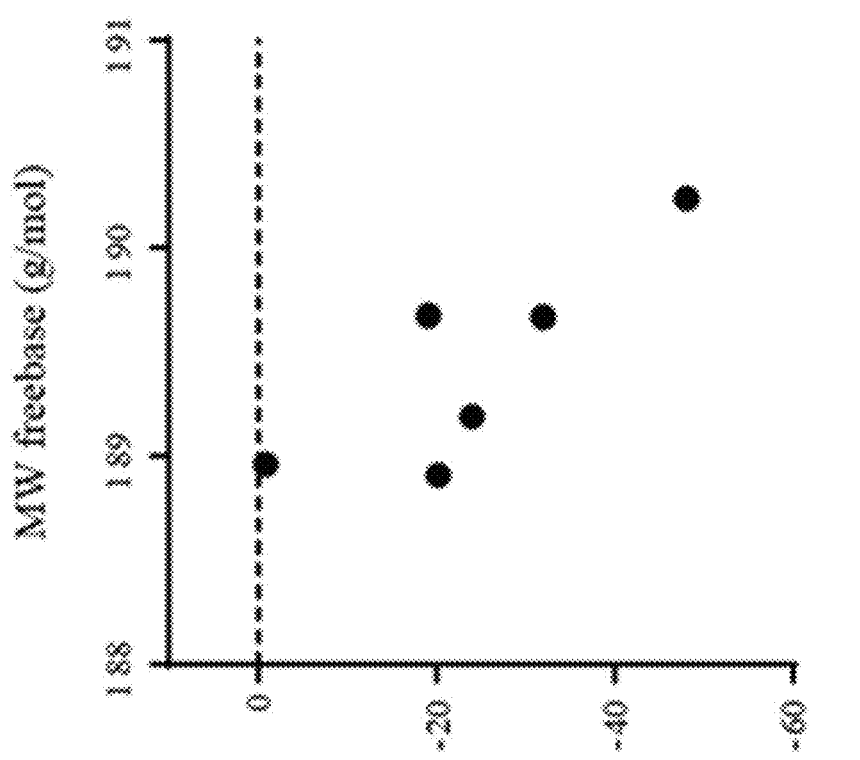
FIG. 3 In vitro intrinsic clearance for DMT and 6 deuterium-containing compositions described in Example 1. A) Linear regression analysis. The $r^2$ value for intrinsic clearance is 0.7648; where the slope was found to be significantly different to zero, p=0.01. B) Intrinsic clearance of deuterated analogues as a percent change from (undeuterated) DMT (dashed line).
Figure 3:
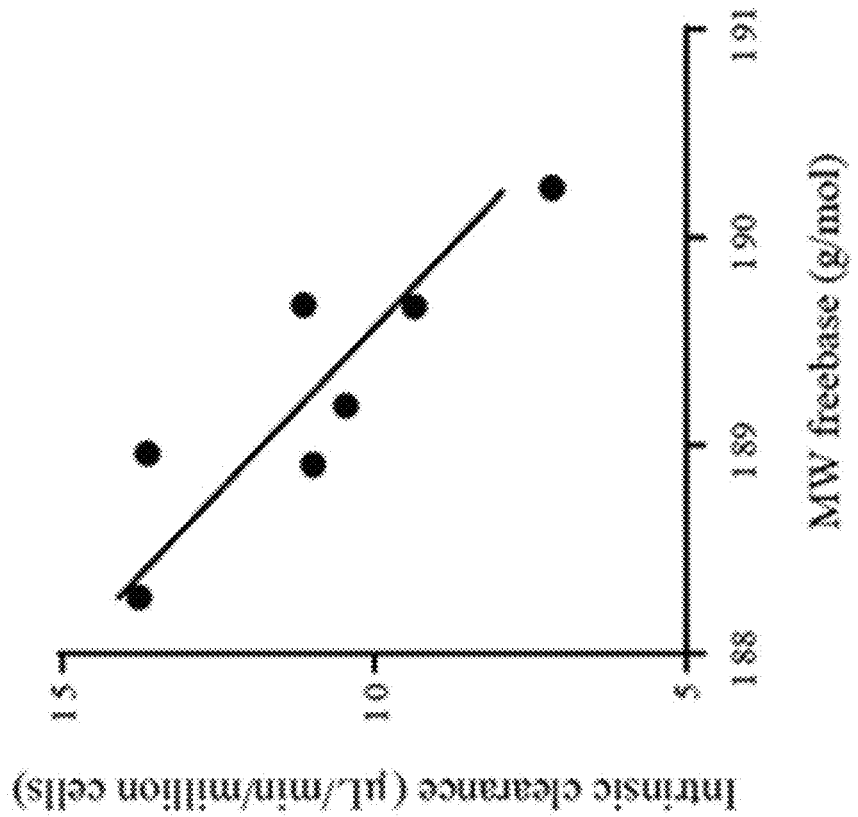

In particular, as detailed in Example 1 and related FIGS. 2 and 3, the inventors have demonstrated that increasing deuterium enrichment at the α-carbon of N,N-dimethyltryptamine increases metabolic stability, leading to a decrease in clearance and longer half-life, wherein a linear relationship exists between molecular weight and half-life between 188.3 and 190.3 grams per mole, and synergistic primary and secondary kinetic isotope effects provide a predictable relationship between molecular weight and half-life for compounds and compositions of Formula I wherein $R^1$ is H between 188.3 and 196.3 grams per mole.

Such types of composition constitute specific embodiments of the first aspect. According to these specific embodiments, the composition consists essentially of two or three compounds selected from N,N-dimethyltryptamine, α-protio, α-deutero-N,N-dimethyltryptamine and α,α-dideutero-N,N-dimethyltryptamine, the composition optionally being in the form of a pharmaceutically acceptable salt, wherein the mean molecular weight of N,N-dimethyltryptamine, α-protio, α-deutero-N,N-dimethyltryptamine and α,α-dideutero-N,N-dimethyltryptamine present in the composition is from 188.28 to 190.28.

According to additional specific aspects, the composition consists essentially of one, two or three compounds selected from N,N-bis(trideutero)dimethyltryptamine (Compound 5), α-protio, α-deutero-N,N-bis(trideutero)dimethyltryptamine (Compound 2) and α,α-dideutero-N,N-bis(trideutero)dimethyltryptamine (Compound 1), said compounds optionally being in the form of a pharmaceutically acceptable salt, wherein the molecular weight or mean molecular weight of N,N-bis(trideutero)dimethyltryptamine, α-protio, α-deutero-N,N-bis(trideutero)dimethyltryptamine, and α,α-dideutero-N,N-bis(trideutero)dimethyltryptamine, present in the composition is from 188.9 to 196.3. In preferred embodiments of this aspect, the composition consists essentially of one compound selected from N,N-bis(trideutero)dimethyltryptamine (Compound 5), preferably α-protio, α-deutero-N,N-bis(trideutero)dimethyltryptamine (Compound 2) and more preferably α,α-dideutero-N,N-bis(trideutero)dimethyltryptamine (Compound 1) in order of increasing metabolic stability.

As used herein, mean molecular weight means the weighted average of molecular weights of the of the N,N-dimethyltryptamine compounds, α-protio, α-deutero-N,N-dimethyltryptamine compounds and α,α-dideutero-N,N-dimethyltryptamine compounds, as measured by an appropriate mass spectroscopic technique, for example LC-MS SIM (selected-ion monitoring), ignoring any weight contribution by formation of pharmaceutically acceptable salts, where applicable.

It will be understood that providing compositions with such specific mean molecular weights can be achieved by those skilled in the art through the teachings herein, in particular by adjusting the relative proportions of lithium aluminium hydride: lithium aluminium deuteride used in Stage 2 when varying the level of deuteration at the alpha position, and by adjusting the relative proportions of dimethylamine:deuterated dimethylamine used in Stage 1 when varying the level of deuteration at the N,N-dimethyl position.

In this context, by reciting that the composition consists essentially of the mixture of N,N-dimethyltryptamine and one or both of α-protio, α-deutero-N,N-dimethyltryptamine and α,α-dideutero-N,N-dimethyltryptamine means that the composition may comprise additional components to these but that the presence of such additional components will not materially affect the essential characteristics of the composition. In particular, the composition will not comprise material quantities of other pharmaceutically active compounds, including other N,N-dimethyltryptamine compounds. Thus material quantities of other deuterated N,N-dimethyltryptamine compounds, in particular β-protio, β-deutero-N,N-dimethyltryptamine compounds and β,β-dideutero-N,N-dimethyltryptamine compounds, such as β-protio, β-deutero-N,N-dimethyltryptamine and β,β-dideutero-N,N-dimethyltryptamine and β-protio, β-deutero-N,N-dimethyltryptamine compounds and β,β-dideutero-N,N-dimethyltryptamine compounds having respectively one or two deuterium atoms in place of hydrogen atoms at the α position are not present in compositions of such embodiments.

In other words, and alternatively put, the compositions according to one specific embodiment constitute a drug substance comprising a biologically active ingredient consisting essentially of one or more of N,N-dimethyltryptamine, α-protio, α-deutero-N,N-dimethyltryptamine and α,α-dideutero-N,N-dimethyltryptamine, wherein the biologically active ingredient has a mean molecular weight from 188.3 to 190.3 and wherein the compounds comprised in the drug substance are optionally in the form of a pharmaceutically acceptable salt. The compositions according to a second specific embodiment constitute a biologically active ingredient consisting essentially of one or more of N,N-bis(trideutero)dimethyltryptamine (Compound 5), α-protio, α-deutero-N,N-bis(trideutero)dimethyltryptamine (Compound 2) and α,α-dideutero-N,N-bis(trideutero)dimethyltryptamine (Compound 1), wherein the biologically active ingredient has a mean molecular weight from 188.9 to 196.3 and wherein the drug substance is optionally in the form of a pharmaceutically acceptable salt.

It will be understood that the compositions according to these specific embodiments comprise one or more of α-protio, α-deutero-N,N-dimethyltryptamine compounds and α,α-dideutero-N,N-dimethyltryptamine compounds in amounts greater than found in isotopically unenriched N,N-dimethyltryptamine. It will also be understood that the greater the proportion of α-protio, α-deutero-N,N-dimethyltryptamine compounds and α,α-dideutero-N,N-dimethyltryptamine compounds in these specific embodiments, the higher the mean molecular weight of the composition.

According to more specific embodiments, the mean molecular weight of N,N-dimethyltryptamine, α-protio, α-deutero-N,N-dimethyltryptamine and α,α-dideutero-N,N-dimethyltryptamine present in the composition is from 188.9 to 189.7, for example 188.90 to 189.70.

According to still more specific embodiments of the specific embodiments described herein, including compositions in which the mean molecular weight of N,N-dimethyltryptamine, α-protio, α-deutero-N,N-dimethyltryptamine and α,α-dideutero-N,N-dimethyltryptamine present in the composition is from 188.9 to 189.7, the compounds comprised in the composition optionally are in the form of a pharmaceutically acceptable salt, by which it will be understood that the N,N-dimethyltryptamine, α-protio, α-deutero- N,N-dimethyltryptamine and α,α-dideutero-N,N-dimethyltryptamine present in the composition are present in pharmaceutically acceptable salt form. Such salts may be as described elsewhere herein and, according to yet more specific embodiments, the composition is in the form of a fumarate salt.

Methods by which the compounds of Formula I may be produced are described below and are suitable for the production of high purity compounds of Formula I. In some embodiments, the compound of Formula I, or a pharmaceutically acceptable salt thereof, is of a purity of between 99% and 100% by HPLC, such as a purity of between 99.5% and 100% by HPLC. In some embodiments, the compound of Formula I, or a pharmaceutically acceptable salt thereof, is of a purity of between 99.9% and 100% by HPLC, such as a purity of between 99.95% and 100% by HPLC.

In some embodiments, the compound of Formula I, or a pharmaceutically acceptable salt thereof, produces two or fewer impurity peaks by HPLC. In some embodiments, where the compound of Formula I, or a pharmaceutically acceptable salt thereof, produces impurity peaks by HPLC, no impurity peak is greater than 0.2%. In some embodiments, no impurity peak by HPLC is greater than 0.1%.

In some embodiments, the compound of Formula I is in the form of a pharmaceutically acceptable salt. The pharmaceutically acceptable salt often comprises a compound of Formula I and a suitable acid. The compound of Formula I is typically protonated at —N($R^2R^3$)$_2$, forming —[NH$R^2R^3$]$^+$, and the resultant positive charge is countered by an anion.

P. H. Stahl and C. G. Wermuth provide an overview of pharmaceutical salts and the acids comprised therein in Handbook of Pharmaceutical Salts: Properties, Selection and Use, Weinheim/Zürich:Wiley-VCH/VHCA, 2002. The acids described in this review are suitable components of the pharmaceutically acceptable salt of Formula I.

In some embodiments, the acid is any one selected from the group consisting of fumaric acid, tartaric acid, citric acid, hydrochloric acid, acetic acid, lactic acid, gluconic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid, aspartic acid, benzenesulfonic acid, benzoic acid, camphoric acid, camphor-10-sulfonic acid, decanoic acid, hexanoic acid, octanoic acid, carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, glucuronic acid, glutamic acid, glutaric acid, glycerophosphoric acid, glycolic acid, hippuric acid, hydrobromic acid, isobutyric acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (-L), salicylic acid, sebacic acid, stearic acid, succinic acid, sulfuric acid, thiocyanic acid, toluenesulfonic acid and undecylenic acid.

Often, the acid is any one selected from fumaric acid, tartaric acid, citric acid and hydrochloric acid. In some embodiments, the acid is fumaric acid, e.g., the pharmaceutically acceptable salt is a fumarate salt.

Also disclosed herein is a synthetic method for making a compound of Formula I or a pharmaceutically acceptable salt thereof. The method comprises Stage 2 and optionally Stage 1, wherein Stage 1 comprises:

(i) reacting a compound of Formula III with two or more coupling agents to produce an activated compound;
(ii) reacting the activated compound with an amine having the formula ($R^2$)$_2$NH to produce a compound of Formula II;
and wherein Stage 2 comprises reacting the compound of Formula II with LiAlD$_4$ or LiAlH$_4$ and LiAlD$_4$,

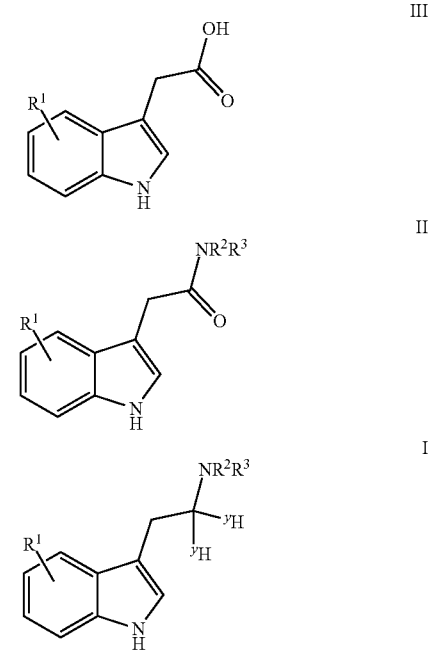

wherein:
each $R^1$ is independently selected from H and D;
$R^2$ is selected from CH$_3$ and CD$_3$;
$R^3$ is selected from CH$_3$ and CD$_3$;
each $^yH$ is independently selected from H and D.

For the avoidance of doubt, embodiments related to the compound of Formula I, or a pharmaceutically acceptable salt thereof, of the first aspect also apply mutatis mutandis to the compound of Formula I (and thus compounds of formulae III and II) of the synthetic method.

The synthetic method avoids the use of problematic oxalyl chloride and employs compounds of Formula III, which may be derived from auxin derivatives. High quality and purity auxins of Formula III are commercially available at scale and/or can be readily synthesised via the Fischer synthesis, Bartoli synthesis, Japp-Klingemann synthesis or Larock synthesis (see, for example, M. B. Smith and J. March, 2020, *March's Advanced Organic Chemistry*, 8$^{th}$ edition, Wiley, N.J.). The method is efficient, scalable, compatible with Current Good Manufacturing Practices (cGMP), and is suitable for the production of high purity compounds of Formula I. For example, the method is suitable for the production of compounds of Formula I in batch scales ranging from 1 g to 100 kg and is suitable for the production of compounds of Formula I with a purity of >99.9% and overall yield of 65% or more.

The compound of Formula II is produced on reacting a compound of Formula III with two or more coupling agents to produce an activated compound, and reacting the activated compound with an amine having the formula $R^2R^3$NH. Without wishing to be bound by theory, it is understood that the nitrogen atom of the amine binds to the carbon atom of the carbonyl of Formula III, resulting in the formation of the compound of Formula II. For the avoidance of doubt, the $R^2$ and $R^3$ groups of formulae II and I are derived from the $R^2$ and $R^3$ groups of the amine. Thus, as described above, $R^2$ and $R^3$ of formulae II and I are independently selected from $CH_3$ and $CD_3$.

The compound of Formula I is produced on reacting the compound of Formula II with $LiAlD_4$ or $LiAlH_4$ and $LiAlD_4$. Without wishing to be bound by theory, it is understood that the hydride or deuteride ions provided by $LiAlD_4$ or $LiAlH_4$ and $LiAlD_4$ bind to the carbon atom of the carbonyl of Formula II, resulting in the formation of the compound of Formula I. For the avoidance of doubt, the $^xH$ groups of Formula I are derived from the hydride or deuteride ions provided by $LiAlD_4$ or $LiAlH_4$ and $LiAlD_4$.

As described above, the method comprises Stage 1 and Stage 2. Stage 1 comprises:

(i) reacting a compound of Formula III with two or more coupling agents to produce an activated compound; and (ii) reacting the activated compound with an amine having the formula $R^2R^3NH$ to produce a compound of Formula II.

The term "coupling agent" refers to an agent which facilitates the chemical reaction between an amine and a carboxylic acid. The two or more coupling agents may comprise a carboxylic acid activating agent, e.g., an agent which reacts with the carboxylic acid moiety of Formula III to produce a compound comprising an activated moiety derived from the original carboxylic acid moiety that is more likely to react with an amine than the original carboxylic acid moiety.

The activated compound is the product of the reaction between the compound of Formula III and the two or more coupling agents. Where the two or more coupling agents comprise carboxylic acid activating agents, the activated compound comprises an activated moiety, derived from the original carboxylic acid moiety of Formula III, which is more likely to react with an amine than the original carboxylic acid moiety.

The two or more coupling agents may comprise a carboxylic acid activating agent. The two or more coupling agents may comprise an additive coupling agent.

An additive coupling agent (also referred to herein as an "additive") is an agent which enhances the reactivity of a coupling agent. The additive may be a compound capable of reacting with the product of the reaction of Formula III and the coupling agent (the product being a compound comprising an activated moiety) to produce a compound comprising an even more activated moiety that is more likely to react with an amine than the original activated moiety.

The additive may be capable of reacting with the product of the reaction of Formula III and the coupling agent (the product being a compound comprising an activated moiety) to produce an activated compound comprising an even more activated moiety that is more likely to react with an amine than the original activated moiety.

Often, the two or more coupling agents comprise a carboxylic acid activating agent and an additive coupling agent.

At least one of the two or more coupling agents may be selected from the group consisting of carbodiimide coupling agents, phosphonium coupling agents and 3-(diethoxy-phosphoryloxy)-1,2,3-benzo[d]triazin-4(3H)-one (DEPBT), such as a carbodiimide coupling agent or a phosphonium coupling agent. At least one of the two or more coupling agents may be a carbodiimide coupling agent.

A carbodiimide coupling agent is a coupling agent which comprises a carbodiimide group R'—N=C=N—R", wherein R' and R" are hydrocarbyl groups optionally substituted with heteroatoms selected from nitrogen, sulfur and oxygen, typically nitrogen. Often, R' and R" are independently selected from $C_1$-$C_6$alkyl, $C_5$-$C_6$cycloalkyl, $C_1$-$C_6$alkylamino and morpholino$C_1$-$C_6$alkyl. Often, $C_1$-$C_6$alkyl is $C_3$alkyl, $C_5$-$C_6$cycloalkyl is cyclohexyl, $C_1$-$C_6$alkylamino is dimethylaminopropyl and/or morpholino$C_1$-$C_6$alkyl is morpholinoethyl.

The carbodiimide coupling agent may be any one selected from the group consisting of dicyclohexylcarbodiimide (DCC), diisopropylcarbodiimide (DIC), (N-(3-Dimethylaminopropyl)-N'-ethylcarbodiimide (EDC) and 1-cyclohexyl-(2-morpholinoethyl)carbodiimide metho-p-toluene sulfonate (CMCT). The carbodiimide coupling agent may be any one selected from the group consisting of dicyclohexylcarbodiimide (DCC), diisopropylcarbodiimide (DIC) and (N-(3-Dimethylaminopropyl)-N'-ethylcarbodiimide (EDC). Often, the carbodiimide coupling agent is N-(3-Dimethylaminopropyl)-N'-ethylcarbodiimide (EDC), typically as a hydrochloride salt (EDC.HCl). EDC or EDC.HCl are particularly preferred as they are non-toxic and are highly water soluble, facilitating their virtually complete removal in workup and wash steps of Stage 1.

A phosphonium coupling agent comprises a phosphonium cation and a counterion, typically a hexafluorophosphate anion. The phosphonium cation may be of Formula $[PR^a{}_3R^b]^+$ wherein Ra is di($C_1$-$C_6$)alkylamino or pyrrolidinyl and $R^b$ is halo or a hydrocarbyl group optionally substituted with nitrogen and/or oxygen atoms. Often, $R^b$ is bromo, benzotriazol-1-yloxy or 7-aza-benzotriazol-1-yloxy.

The phosphonium coupling agent may be any one selected from the group consisting of benzotriazol-1-yloxy-tris(dimethylamino)-phosphonium hexafluorophosphate (BOP), bromo-tripyrrolidino-phosphonium hexafluorophosphate (PyBrOP), benzotriazol-1-yloxy-tripyrrolidino-phosphonium hexafluorophosphate (PyBOP), 7-aza-benzotriazol-1-yloxy-tripyrrolidinophosphonium hexafluorophosphate (PyAOP) and ethyl cyano(hydroxyimino)acetato-$O_2$) tri-(1-pyrrolidinyl)-phosphonium hexafluorophosphate (PyOxim).

At least one of the two or more coupling agents may be an additive coupling agent selected from the group consisting of 1-hydroxybenzotriazole (HOBt), hydroxy-3,4-dihydro-4-oxo-1,2,3-benzotriazine (HOOBt), N-hydroxysuccinimide (HOSu), 1-hydroxy-7-azabenzotriazole (HOAt), ethyl 2-cyano-2-(hydroximino)acetate (Oxyma Pure), 4-(N,N-Dimethylamino)pyridine (DMAP), N-hydroxy-5-norbornene-2,3-dicarboximide (HONB), 6-chloro-1-hydroxybenzotriazole (6-Cl-HOBt), 3-hydroxy-4-oxo-3,4-dihydro-1,2,3-benzotriazine (HODhbt), 3-hydroxy-4-oxo-3,4-dihydro-5-azabenzo-1,2,3-triazene (HODhat) and 3-hydroxyl-4-oxo-3,4-dihydro-5-azepine benzo-1,3-diazines (HODhad).

At least one of the two or more coupling agents may be an additive coupling agent selected from the group consisting of 1-hydroxybenzotriazole (HOBt), hydroxy-3,4-dihydro-4-oxo-1,2,3-benzotriazine (HOOBt), N-hydroxysuccinimide (HOSu), 1-hydroxy-7-azabenzotriazole (HOAt), ethyl 2-cyano-2-(hydroximino)acetate (Oxyma Pure) and 4-(N,N-Dimethylamino)pyridine (DMAP).

At least one of the two or more coupling agents may be an additive coupling agent which is 1-hydroxybenzotriazole.

The two or more coupling agents may consist of a coupling agent and an additive coupling agent wherein the coupling agent and additive coupling agent may be as described in the above embodiments.

A benefit of using both a coupling agent and an additive coupling agent is an increased rate of formation of compounds of Formula II from compounds of Formula III and an amine having the formula $(R^2)_2NH$. In addition, when an additive coupling agent is used together with a carbodiimide coupling agent, the likelihood of unwanted side reactions may be reduced. For example, reaction of a compound of Formula III with a carbodiimide coupling reagent is likely to form an O-acylisourea. This may undergo a rearrangement to form an N-acylurea, which is a stable compound unlikely to react with an amine. Additive coupling reagents may react with O-acylureas before rearrangement to N-acylureas, and produce compounds that go on to react with an amine, rather than inactive N-acylureas.

Therefore, the two or more coupling agents may consist of a carbodiimide coupling agent and an additive coupling agent.

The two or more coupling agents may consist of N-(3-Dimethylaminopropyl)-N'-ethylcarbodiimide (EDC), typically as a hydrochloride salt (EDC.HCl), and 1-hydroxybenzotriazole (HOBt).

Often, an excess of coupling agent with respect to compound of Formula III is used. The ratio of coupling agent:compound of Formula III may be about 1:1 to about 3:1, typically about 1:1 to about 2:1 and most typically about 1:1 to about 1.5:1.

Often, an excess of additive coupling agent with respect to compound of Formula III is used. Sometimes, the ratio of additive coupling agent:compound of Formula III is about 1:1 to about 3:1, typically about 1:1 to about 2:1 and most typically about 1:1 to about 1.5:1.

Where the two or more coupling agents comprise a coupling agent and an additive coupling agent, a ratio of coupling agent:compound of Formula III and additive coupling agent:compound of Formula III of about 1:1 to about 1.5:1 may be used.

As described above, Stage 1 comprises reacting the activated compound (the product of reacting a compound of Formula III with two or more coupling agents) with an amine having the formula $R^2R^3NH$ to produce a compound of Formula II. $R^2$ and $R^3$ of formulae II and I are independently selected from $CH_3$ and $CD_3$.

The ratio of amine:compound of Formula III employed in the method is often about ≥1:1. Sometimes, the ratio of amine:compound of Formula III is about 1:1 to about 3:1, typically about 1:1 to about 2:1.

Sometimes, Stage 1 further comprises isolating the compound of Formula II. The skilled person is aware of techniques in the art suitable for isolation of a compound of Formula II. For example, a compound of Formula II may be extracted into an organic solvent such as dichloromethane or ethyl acetate, washed with an aqueous solution such as an aqueous basic solution, and concentrated. To increase purity, the isolated compound of Formula II may be recrystallized. The skilled person is aware of techniques that are suitable for recrystallisation of compounds of Formula II. For example, the compound of Formula II may be dissolved in the minimum amount of solvent at a particular temperature (e.g., at ambient temperature (e.g., 15 to 25° C.) or at elevated temperatures where heat is applied to the solution) and the resultant solution cooled to encourage precipitation. Alternatively, or in addition, the volume of the solution may be reduced to encourage precipitation, e.g., by simple evaporation at ambient temperature and pressure. Alternatively, or in addition, an anti-solvent may be used (in which the compound of Formula II is less soluble than the solvent already present).

Isolated compounds of Formula II are stable and may be stored as solids at ambient temperature, e.g., at about 20° C., in the air. They may, but need not be, stored under inert conditions, e.g., under nitrogen or argon, or at reduced temperatures, e.g., in a refrigerator or freezer.

Typically, steps (i) and (ii) of Stage 1 are carried out in a suitable solvent. The skilled person is able to assess which solvents are suitable for these steps. Examples of suitable solvents include dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). In some embodiments, steps (i) and (ii) of Stage 1 are carried out in dichloromethane.

Steps (i) and (ii) of Stage 1 are carried out at a suitable temperature and the skilled person is able to assess which temperatures are suitable for these steps. Often, steps (i) and (ii) of Stage 1 are carried out at temperatures of about 10° C. to about 30° C. In some embodiments, steps (i) and (ii) of Stage 1 are carried out at room temperature (about 20° C.).

Sometimes, Stage 1 of the method comprises the steps of:
(i) contacting a compound of Formula III and between 1 and 1.5 equivalents of an additive coupling agent, and between 1 and 1.5 equivalents of a carbodiimide coupling agent to produce a first composition; and
(ii) contacting the first composition with between 1 and 2 equivalents of an amine having the formula $R^2R^3NH$ to produce a second composition.

Often, 1 g or more, such as 1 g to 100 kg or 1 g to 1 kg of a compound of Formula III is employed in the method.

The contacting of steps i. and ii. is often carried out in the presence of a first solvent, such as between 5 and 20 volumes of a first solvent. The first solvent may be selected from any one of dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). Typically, the first solvent is DCM.

Often, step i. further comprises stirring or agitating the first composition. The first composition may be stirred or agitated for at least 30 minutes, such as 30 minutes to 3 hours or 30 minutes to 2 hours, preferably at least 1 hour, for example 1 to 3 hours or 1 to 2 hours. The first composition may be maintained at a temperature of between 10° C. and 30° C.

The amine of step ii. is often dissolved in a solvent, such as tetrahydrofuran (THF) or ether, prior to contacting. The amine may be present in the solvent at a concentration of about 2 M. Typically, the amine of step ii. is dissolved in THF.

Sometimes, step ii. further comprises stirring or agitating the second composition. The second composition may be stirred or agitated for at least 30 minutes, such as 30 minutes to 3 hours or 30 minutes to 2 hours, preferably at least 1 hour, for example 1 to 3 hours or 1 to 2 hours. The second composition may be maintained at a temperature of between 10° C. and 30° C.

Step ii. may further comprise contacting the second composition with an aqueous basic solution to produce a third composition, for example contacting the second composition with between 2 and 10 volumes of an aqueous basic solution such as an aqueous solution comprising potassium carbonate.

Sometimes, step ii. further comprises stirring or agitating the third composition. The third composition may be stirred or agitated for at least 1 minute, such as 1 to 15 minutes or 1 to 10 minutes, preferably at least 5 minutes, for example 5 to 15 minutes or 5 to 10 minutes. The third composition may be maintained at a temperature of between 10° C. and 30° C.

Where the third composition comprises an organic and an aqueous component, step ii. may further comprise separating the organic component from the aqueous component. The organic component may be separated from the aqueous component within 8 hours of the contacting of step i.

Sometimes, Stage 1 of the method comprises the steps of:
i. adding to a first vessel 1 g or more of a compound of Formula III and between 1 and 1.5 equivalents of an additive coupling agent,
ii. adding to the first vessel between 5 and 20 volumes of a first solvent selected from DCM, acetone, IPA, iPrOAc, TBME, 2-MeTHF and EtOAc,
iii. adding to the first vessel between 1 and 1.5 equivalents of a carbodiimide coupling agent,
iv. stirring the contents of the first vessel for at least 30 minutes, preferably at least 1 hour (such as 1 to 2 hours), at between 10° C. and 30° C.,
v. adding to the first vessel between 1 and 2 equivalents of an amine having the formula $R^2R^3NH$, wherein the amine is preferably dissolved in an ether solvent,
vi. further stirring the contents of the first vessel for at least 30 minutes, preferably at least 1 hour (such as 1 to 2 hours), at between 10° C. and 30° C.,
vii. adding to the first vessel between 2 and 10 volumes of an aqueous basic solution,
viii. further stirring the contents of the first vessel for at least 1 minute, preferably at least 5 minutes (such as 5 to 10 minutes), at between 10° C. and 30° C.,
ix. allowing an immiscible organic fraction to separate from an aqueous fraction, wherein the organic fraction comprises the compound of Formula II, and
x. removing the organic fraction comprising the compound of Formula II, wherein steps i. to x. are carried out within a single 8 hour period.

Often, the first solvent is DCM.

Often, the amine is dimethylamine. The amine may be dissolved in THF, for example at a concentration of 2 M.

Often, the aqueous basic solution comprises potassium carbonate.

Sometimes, Stage 1 of the method further comprises the steps of:
xi. drying the organic fraction with a drying agent, for example a drying agent selected from calcium chloride, magnesium sulphate, and sodium sulphate,
xii. filtering the organic fraction,
xiii. concentrating the organic fraction, for example under vacuum such as under a pressure of less than 1 atmosphere,
xiv. adding the concentrated organic fraction to a second vessel,
xv. adding between 2 and 10 volumes of a second solvent to the second vessel, wherein the second solvent is selected from IPA, EtOAc, IPrOAc, acetonitrile (MeCN), TBME, THF, 2-MeTHF and toluene,
xvi. stirring the contents of the second vessel for at least 1 hour, preferably at least 2 hours (such as 2 to 3 hours), at temperatures of between 45° C. and 55° C.,
xvii. cooling the contents of the second vessel to temperatures of between 15° C. and 25° C.,
xviii. filtering contents of the second vessel to obtain a filtrate, wherein the filtrate comprises the compound of Formula II, and
xix. drying the filtrate.

The drying agent of step xi. is typically magnesium sulphate. Often, the solvent of step xv. is selected from TBME and IPA.

Stage 2 of the method comprises reacting the compound of Formula II with $LiAlD_4$ or $LiAlH_4$ and $LiAlD_4$ to produce a compound of Formula I. $LiAlD_4$ or mixtures of $LiAlH_4$ and $LiAlD_4$ may be reacted with the compound of Formula II. In preferred embodiments, Stage 2 of the method comprises reacting the compound of Formula II with a mixture of $LiAlH_4$ and $LiAlD_4$. Such mixtures comprise $LiAlD_4$ and comprise between 0.1 and 99.9% hydride. Mixtures of between 2% and 98% lithium aluminium hydride or between 2% and 98% lithium aluminium deuteride may be employed. Sometimes, mixtures of $LiAlH_4$ and $LiAlD_4$ consist essentially of 98% $LiAlD_4$/2% $LiAlH_4$. Sometimes, such mixtures consist essentially of 95% $LiAlD_4$/5% $LiAlH_4$, 95% $LiAlD_4$/5% $LiAlH_4$, 85% $LiAlD_4$/15% $LiAlH_4$, 80% $LiAlD_4$/20% $LiAlH_4$, 75% $LiAlD_4$/25% $LiAlH_4$, 70% $LiAlD_4$/30% $LiAlH_4$, 65% $LiAlD_4$/35% $LiAlH_4$, 60% $LiAlD_4$/40% $LiAlH_4$, 55% $LiAlD_4$/45% $LiAlH_4$, 50% $LiAlD_4$/50% $LiAlH_4$, 45% $LiAlD_4$/55% $LiAlH_4$, 40% $LiAlD_4$/60% $LiAlH_4$, 35% $LiAlD_4$/65% $LiAlH_4$, 30% $LiAlD_4$/70% $LiAlH_4$, 25% $LiAlD_4$/75% $LiAlH_4$, 20% $LiAlD_4$/80% $LiAlH_4$, 15% $LiAlD_4$/85% $LiAlH_4$, 10% $LiAlD_4$/90% $LiAlH_4$, 5% $LiAlD_4$/95% $LiAlH_4$, or 2% $LiAlD_4$/98% $LiAlH_4$.

By the mixtures of $LiAlH_4$ and $LiAlD_4$ consisting essentially of specified percentages of $LiAlH_4$ and $LiAlD_4$ is meant that the mixture may comprise additional components (other than $LiAlH_4$ and $LiAlD_4$) but that the presence of these additional components will not materially affect the essential characteristics of the mixture. In particular, mixtures consisting essentially of $LiAlH_4$ and $LiAlD_4$ will not comprise material amounts of agents that are detrimental to the reduction of compounds of Formula II to produce compounds of Formula I (e.g., material amounts of agents that react with $LiAlH_4$ and $LiAlD_4$, compounds of Formula II and/or compounds of Formula I in a way that inhibits the reduction of compounds of Formula II to produce compounds of Formula I).

The amount of $LiAlH_4$ or $LiAlD_4$ comprised in mixtures of the two depends on the degree of deuteration sought in the compound of Formula I. For example, where compounds of Formula I are sought in which one $^yH$ is protium and the other is deuterium, a mixture of 50% $LiAlH_4$ and 50% $LiAlD_4$ may be preferred. Alternatively, where a mixture of compounds of Formula I are sought, in which approximately half of the compounds comprise two deuterium atoms at the α-position (e.g., both $^yH$ are deuterium) and approximately half of the compounds comprise one deuterium atom and one protium atom at the α-position (e.g., one $^yH$ is deuterium and the other is protium), a mixture of 25% $LiAlH_4$ and 75% $LiAlD_4$ may be preferred.

The amount of $LiAlD_4$ or $LiAlH_4$ and $LiAlD_4$ employed relative to compound of Formula II is often 1:1. For the avoidance of doubt, the ratios of $LiAlD_4$ or $LiAlH_4$ and $LiAlD_4$ relative to compound of Formula II refer to the total amount of $LiAlD_4$ or $LiAlH_4$ and $LiAlD_4$ used with respect to the amount of compound II. Sometimes, the ratio of $LiAlD_4$ or $LiAlH_4$ and $LiAlD_4$:compound of Formula II is 0.5:1 to 1:1, such as 0.8:1 to 1:1. Typically, the ratio of $LiAlH_4$ and/or $LiAlD_4$:compound of Formula II is 0.9:1.

Typically, Stage 2 of the method is carried out in a suitable solvent. The skilled person is able to assess which solvents are suitable for Stage 2. Examples of suitable solvents include ethers such as THF and diethyl ether. Often, Stage 2 is carried out in THF.

Often, the $LiAlD_4$ or $LiAlH_4$ and $LiAlD_4$ is provided as a solution or suspension of $LiAlD_4$ or $LiAlH_4$ and $LiAlD_4$ in a suitable solvent such as an ether, for example THF or diethyl ether, typically THF.

Stage 2 of the method is carried out at a suitable temperature and the skilled person is able to assess which temperatures are suitable for these steps. Often, Stage 2 is carried out at temperatures of about −5° C. to about 65° C.

Typically, Stage 2 further comprises isolating the compound of Formula I. The skilled person is aware of techniques in the art suitable for isolation of a compound of Formula I. For example, on quenching the reaction (e.g., with an aqueous solution of a tartrate salt such as Rochelle's salts), a compound of Formula I may be extracted into an organic solvent such as an ether, e.g., THF or diethyl ether, washed with an aqueous solution such as an aqueous basic solution, and concentrated. The isolated compound of Formula I may be recrystallized. The skilled person is aware of techniques that are suitable for recrystallisation of a compound of Formula I. The examples of recrystallisation techniques described with respect to recrystallisation of a compound of Formula II apply mutatis mutandis to recrystallisation of a compound of Formula I.

Often, about 1 g or more, such as about 1 g to about 100 kg or about 1 g to about 1 kg of a compound of Formula II is employed in the method.

Typically, Stage 2 of the method comprises contacting a compound of Formula II and between about 0.8 and about 1 equivalents, such as about 0.9 equivalents of $LiAlD_4$ or $LiAlH_4$ and $LiAlD_4$ to produce a first composition.

The contacting is typically carried out in the presence of a solvent such as an ether, e.g., THF or diethyl ether, typically THF.

Often, the contacting comprises dropwise addition of $LiAlD_4$ or $LiAlH_4$ and $LiAlD_4$ to a compound of Formula II, wherein $LiAlD_4$ or $LiAlH_4$ and $LiAlD_4$ is provided as a solution or suspension of $LiAlD_4$ or $LiAlH_4$ and $LiAlD_4$ in a suitable solvent, such as an ether, e.g., THF or diethyl ether. The $LiAlD_4$ or $LiAlH_4$ and $LiAlD_4$ may be provided as a 2.4 M or 2 M solution or suspension of $LiAlD_4$ or $LiAlH_4$ and $LiAlD_4$ in THF. Sometimes, the $LiAlD_4$ or $LiAlH_4$ and $LiAlD_4$ is provided as a 2 M solution or suspension of $LiAlD_4$ or $LiAlH_4$ and $LiAlD_4$ in THF.

The contacting is often carried out at temperatures of about −5° C. to about 65° C.

Often, Stage 2 further comprises stirring or agitating the first composition. The first composition may be stirred or agitated for about 1 hour to about 6 hours, typically for about 2 hours. The first composition may be stirred or agitated at a temperature of about 55° C. to about 65° C. Often, the first composition is stirred or agitated at a temperature of about 55° C. to about 65° C. and then cooled to temperatures of about 10° C. to about 30° C.

Typically, the compound of Formula II is contacted with about 0.9 equivalents of $LiAlD_4$ or $LiAlH_4$ and $LiAlD_4$.

Stage 2 of the method may comprise the steps of:
i. adding to a third vessel 1 g or more (such as 1 g to 1 kg) of a compound of Formula II,
ii. adding to the third vessel between 5 and 20 volumes of an ether solvent,
iii. adding to the third vessel, dropwise over at least 15 minutes (e.g., 15 to 30 minutes), a solution of between 0.8 and 1 equivalents of $LiAlD_4$ or $LiAlH_4$ and $LiAlD_4$ in the ether solvent at a temperature of between −5° C. and 65° C.,
iv. stirring the contents of the third vessel at between 55° C. and 65° C. for between 1 hour and 6 hours, preferably 2 hours, and
v. cooling the contents of the third vessel to between 10° C. and 30° C., wherein the contents of the third vessel comprise a compound of Formula I.

Often, the ether solvent is THF. Typically, 0.9 equivalents of $LiAlD_4$ or $LiAlH_4$ and $LiAlD_4$ are added to the third vessel in step iii. The $LiAlD_4$ or $LiAlH_4$ and $LiAlD_4$ is typically added to the third vessel as a 2.4 M or 2 M solution in THF. Sometimes, the $LiAlD_4$ or $LiAlH_4$ and $LiAlD_4$ is added to the third vessel as a 2 M solution in THF.

Sometimes, Stage 2 of the method comprises a workup comprising the steps of:
vi. adding between 5 and 20 volumes of an aqueous solution of a tartrate salt (such as Rochelle's salts) to a fourth vessel,
vii. adding a composition comprising crude compound of Formula I, over at least 15 minutes (such as 15 minutes to 1 hour), preferably at least 30 minutes (such as 30 minutes to 1 hour), to the fourth vessel at between 15° C. and 25° C., and
viii. stirring the contents of the fourth vessel at between 15° C. and 25° C. for at least 30 minutes (such as 30 minutes to 1 hour).

For the avoidance of doubt, the composition comprising crude compound of Formula I refers to the contents of the third vessel on completion of step v. of Stage 2, described above.

Stage 2 of the method may further comprise the steps of:
ix. allowing an organic fraction to separate from an aqueous fraction, wherein the organic fraction comprises the compound of Formula I,
x. removing the aqueous fraction from the fourth vessel,
xi. adding between 5 and 20 volumes of a brine solution to the fourth vessel,
xii. stirring the contents of the fourth vessel at a temperature between 15° C. and 25° C. for at least 5 minutes (such as 5 to 15 minutes),
xiii. removing the organic fraction comprising the compound of Formula I as a freebase,
xiv. drying the organic fraction using a drying agent, such as a drying agent selected from calcium chloride, magnesium sulphate, and sodium sulphate,
xv. filtering the organic fraction, and
xvi. concentrating the organic fraction, for example under vacuum such as under a pressure of less than 1 atmosphere.

Isolated compounds of Formula I (produced via Stage 2) are stable and may be stored as solids at ambient temperature, e.g., at about 20° C., in the air. They may, but need not be, stored under inert conditions, e.g., under nitrogen or argon, or at reduced temperatures, e.g., in a refrigerator or freezer. Sometimes, the compound of Formula I is stored in a solvent, for example dissolved in ethanol. Sometimes, the compound of Formula I is stored in a solvent for more than 8 hours, typically more than 12 hours.

As described above, the compound of Formula I may be in the form of a pharmaceutically acceptable salt. A pharmaceutically acceptable salt may be formed from a compound of Formula I by reaction with a suitable acid. Thus, the method may further comprise a Stage 3, in which the compound of Formula I is reacted with an acidic reagent to produce a pharmaceutically acceptable salt of the compound of Formula I. The acidic reagent may be suitable for crystallising a pharmaceutically acceptable salt of the compound of Formula I.

For the avoidance of doubt, where a reagent is expressed herein as a number of equivalents, this is with respect to the molar equivalents of the compound of Formula III, Formula II or Formula I for reagents in Stage 1, Stage 2 or Stage 3 respectively.

A method of synthesising a compound of Formula I, or a pharmaceutically acceptable salt thereof often comprises Stage 1, Stage 2 and Stage 3, wherein Stage 1 comprises:

(i) reacting a compound of Formula III with two or more coupling agents to produce an activated compound;

(ii) reacting the activated compound with an amine having the formula $R^2R^3NH$ to produce a compound of Formula II; and (iii) isolating the compound of Formula II;

Stage 2 comprises reacting the compound of Formula II with $LiAlD_4$ or $LiAlH_4$ and $LiAlD_4$; and Stage 3 comprises the step of reacting the compound of Formula I with an acidic reagent suitable for crystallising a pharmaceutically acceptable salt of the compound of Formula I.

Sometimes, a ratio of acidic reagent:compound of Formula I of ≥1:1 is used. Often, the ratio of acidic reagent:compound of Formula I is 1:1.

Typically, Stage 3 of the method is carried out in a suitable solvent. The skilled person is able to assess which solvents are suitable for Stage 3. Examples of suitable solvents include ethanol, IPA, iPrOAc and MeCN. Stage 3 is often carried out in ethanol.

Stage 3 of the method is carried out at a suitable temperature and the skilled person is able to assess which temperatures are suitable for these steps.

Stage 3 of the method often comprises contacting a compound of Formula I and an acidic reagent to produce a first composition. Often, the contacting of Stage 3 is carried out at temperatures of 70 to 100° C., for example 70 to 90° C. or 70 to 80° C. Sometimes, the contacting of Stage 3 is carried out at temperatures of about 75° C.

Often, Stage 3 further comprises isolating the pharmaceutically acceptable salt of Formula I. The skilled person is aware of techniques in the art suitable for isolation of such a compound. For example, where the compound is dissolved within a suspension, it may be separated from some of the other components of the suspension via filtration, such as hot filtration. The pharmaceutically acceptable salt of Formula I may precipitate from the filtrate. The skilled person is aware of methods to encourage precipitation of a compound from a solution, such as cooling the solution, concentrating the solution and/or adding into the solution a crystalline form of the compound to encourage nucleation and the growth of further crystals of the compound from the solution (e.g., seeding). The pharmaceutically acceptable salt of Formula I may be recrystallized. The skilled person is aware of techniques that are suitable for recrystallisation of a pharmaceutically acceptable salt of Formula I. The examples of recrystallisation techniques described with respect to recrystallisation of a compound of Formula II apply mutatis mutandis to recrystallisation of a pharmaceutically acceptable salt of Formula I.

Stage 3 of the method may comprise the steps of:
i. adding to a fifth vessel at least one equivalent of an acidic reagent suitable for crystallising a pharmaceutically acceptable salt of a compound of Formula I,
ii. dissolving a compound of Formula I as a freebase in between 5 and 20 volumes of a solvent such as a solvent selected from ethanol, IPA, iPrOAc and MeCN and adding the solution to the fifth reaction vessel,
iii. stirring the contents of the fifth vessel at a temperature of above 72° C. (such as 72 to 90° C.),
iv. filtering the contents of the fifth vessel,
v. adding the filtrate to a sixth vessel and cooling the contents to a temperature of 67° C. to 73° C.,
vi. optionally seeding the sixth vessel with a crystalline form of the pharmaceutically acceptable salt of the compound of Formula I,
vii. stirring the contents of the sixth vessel at a temperature of 67° C. to 73° C. for at least 30 minutes (such as 30 minutes to 1 hour),
viii. cooling the contents of the sixth vessel to a temperature of −5° C. to 5° C. at a rate of 2 to 8° C. per hour, and
ix. filtering the contents of the sixth vessel to produce a filter cake comprising a pharmaceutically acceptable salt of the compound of Formula I.

Often, the solvent of step ii. is ethanol. Often, the rate of cooling in step viii. is 5° C. per hour.

As described above, the pharmaceutically acceptable salt often comprises a compound of Formula I and a suitable acid. The acids listed above as suitable components of the pharmaceutically acceptable salts apply mutatis mutandis to the acidic reagents of Stage 3 of the method Often, the acidic reagent is any one selected from fumaric acid, tartaric acid, citric acid and hydrochloric acid, such as fumaric acid.

The synthetic method disclosed herein is particularly useful for producing therapeutic deuterated substituted dialkyl tryptamines, as the method employs significantly less $LiAlD_4$ than other syntheses known in the art since the method substitutes deuterium at the alpha position but not the beta position. $LiAlD_4$ is among the most expensive and difficult to manufacture reagents in this synthesis. Moreover, optimised methods disclosed herein reduce $LiAlD_4$ or $LiAlH_4$ and $LiAlD_4$ requirements, for example from 2 equivalents to 0.9 equivalents which increases economic efficiency in manufacturing deuterated compounds of Formula I. In view of this, compounds of Formula I are cheaper to make, via the synthetic method disclosed herein, than known deuterated analogues which are typically deuterated at both the alpha and beta position.

The synthetic method disclosed herein is efficient; compounds of Formula I may be produced with an overall yield of between 50% and 100%, such as between 60% and 100% or between 65% and 100%.

Each and every patent and non-patent reference referred to herein is hereby incorporated by reference in its entirety, as if the entire contents of each reference were set forth herein in its entirety.

The invention may be further understood with reference to the following non-limiting examples.

EXAMPLES

Example 1

In the first example, the inventors demonstrate that the primary kinetic isotope effect bestowed upon N,N-dimethyltryptamine when enriched by one or two deuteriums at the alpha position exhibits a linear relationship between mean molecular weight and half-life in human hepatocyte assays. Use of Human Hepatocytes to Assess the In Vitro Intrinsic Clearance of Deuterated DMT Analogue Blends Relative to DMT In vitro determination of intrinsic clearance is a valuable model for predicting in vivo hepatic clearance. The liver is the main organ of drug metabolism in the body, containing both phase I and phase II drug metabolising enzymes, which are present in the intact cell.

Synthesis of Samples

N,N-DMT 220.9 g (as free base) was prepared as N,N-DMT fumarate, using the chemistry depicted in Scheme 1. An additional 4-6 g of six partially deuterated mixtures were also produced using modified conditions.

C. to afford Stage 1 266.2 g (yield=90%) as an off-white solid in a purity of 98.5% by HPLC and >95% by NMR.

Stage 2: preparation of DMT

To a 5 L vessel under $N_2$ was charged Stage 1 (272.5 g, 1.347 mol) and tetrahydrofuran (THF, 1363 mL) to give an off-white suspension. 2.4 M $LiAlH_4$ in THF (505.3 mL, 1.213 mol) was then charged dropwise over 35 minutes at 20-56° C. to give an amber solution. The solution was heated

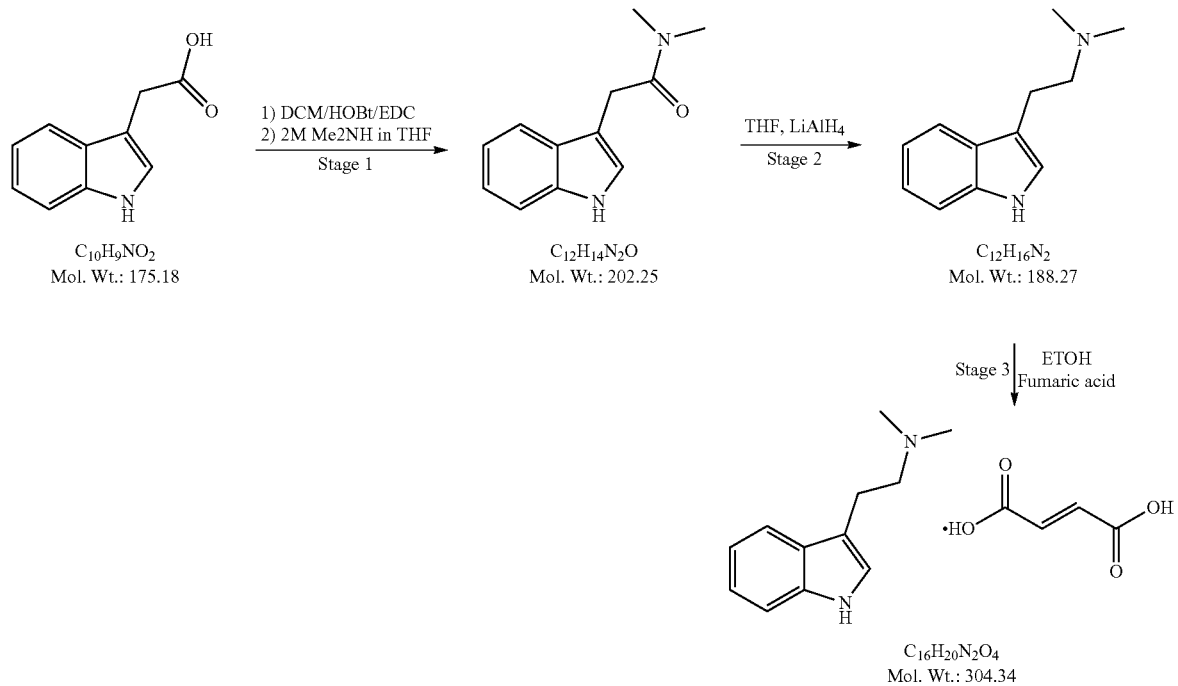

Scheme 1

Synthesis of DMT

Stage 1: Coupling of indole-3-acetic Acid and Dimethylamine

To a 5 L vessel under $N_2$ was charged indole-3-acetic acid (257.0 g, 1.467 mol), hydroxybenzotriazole (HOBt, ~20% wet) (297.3 g, 1.760 mol) and dichloromethane (2313 mL) to give a milky white suspension. 1-Ethyl-3-(3-dimethylaminopropyl) carbodimide hydrochloride (EDC.HCl, 337.5 g, 1.760 mol) was then charged portion-wise over 5 minutes at 16-22° C. The reaction mixture was stirred for 2 hours at ambient temperature before 2M dimethylamine in THF (1100 mL, 2.200 mol) was charged dropwise over 20 minutes at 20-30° C. The resultant solution was stirred at ambient temperature for 1 hour where HPLC indicated 1.1% indole-3-acetic acid and 98.1% target product referred to as Stage 1). The reaction mixture was then charged with 10% $KCO_3$ (1285 mL) and stirred for 5 minutes. The layers were separated, and the upper aqueous layer extracted with dichloromethane (643 mL×2). The organic extracts were combined and washed with saturated brine (643 mL). The organic extracts were then dried over $MgSO_4$, filtered and concentrated in vacuo at 45° C. This provided 303.1 g of crude Stage 1 as an off-white sticky solid. The crude material was then subjected to a slurry in tert-butyl methyl ether (TBME, 2570 mL) at 50° C. for 2 hours before being cooled to ambient temperature, filtered and washed with TBME (514 mL×2). The filter-cake was then dried in vacuo at 50° to 60° C. for 2 hours where HPLC indicated Stage 1 ND, target product bracket referred to as Stage 2, 92.5%), Impurity 1 (2.6%), Impurity 2 (1.9%). The complete reaction mixture was cooled to ambient temperature and then charged to a solution of 25% Rochelle's salts (aq) (2725 mL) dropwise over 30 minutes at 20-30° C. The resultant milky white suspension was allowed to stir at 20-25° C. for 1 hour after which the layers were separated and the upper organic layer washed with saturated brine (681 mL). The organic layer was then dried over $MgSO_4$, filtered and concentrated in vacuo at 45° C. The resultant crude oil was subjected to an azeotrope from ethanol (545 mL×2). This provided 234.6 g (yield=92%) of Stage 2 in a purity of 95.0% by HPLC and >95% by NMR.

Stage 3a (i)-(iii): Preparation of Seed Crystals of DMT Fumarate (i) Stage 2 (100 mg) was taken up in 8 volumes of isopropyl acetate and warmed to 50° C. before charging fumaric acid (1 equivalent) as a solution in ethanol. The flask was then allowed to mature at 50° C. for 1 hour before cooling to room temperature and stirring overnight, resulting in a white suspension. The solids were isolated by filtration and dried for 4 hours at 50° C. to provide 161 mg of product (>99% yield). Purity by HPLC was determined to be 99.5% and by NMR to be >95%.

(ii) Substitution of isopropyl acetate for isopropyl alcohol in method (i) afforded a white suspension after stirring overnight. The solids were isolated by filtration and dried for 4 hours at 50° C. to provide 168 mg of product (>99% yield). Purity by HPLC was determined to be 99.8% and by NMR to be >95%.

Substitution of isopropyl acetate for tetrahydrofuran in method (i) afforded a white suspension after stirring overnight. The solids were isolated by filtration and dried for 4 hours at 50° C. to provide 161 mg of product (>99% yield). Purity by HPLC was determined to be 99.4% and by NMR to be >95%.

Analysis by x-ray powder diffraction, showed the products of each of methods 9i) to (iii) to be the same, which was labelled Pattern A.

Stage 3b: Preparation of DMT Fumarate

To a 5 L flange flask under $N_2$ was charged fumaric acid (152.7 g, 1.315 mol) and Stage 2 (248.2 g, 1.315 mol) as a solution in ethanol (2928 mL). The mixture was heated to 75° C. to give a dark brown solution. The solution was polish filtered into a preheated (80° C.) 5 L jacketed vessel. The solution was then cooled to 70° C. and seeded with Pattern A (0.1 wt %), the seed was allowed to mature for 30 minutes before cooling to 0° C. at a rate of 5° C./hour. After stirring for an additional 4 hours at 0° C., the batch was filtered and washed with cold ethanol (496 mL×2) and then dried at 50° C. overnight. This provided 312.4 g (yield=78%) of Stage 3 in a purity of 99.9% by HPLC and >95% by NMR. XRPD: Pattern A.

Synthesis of Deuterated Mixtures of DMT Compounds

A modified synthesis at Stage 2 using solid $LiAlH_4$/$LiAlD_4$ mixtures was adopted, using 1.8 equivalents of $LiAlH_4$/$LiAlD_4$ versus 0.9 equivalents using the process described above for undeuterated DMT.

Representative synthesis of a deuterated (1:1 $LiAlH_4$:$LiAlD_4$) DMT composition: To a 250 mL 3-neck flask under $N_2$ was charged $LiAlH_4$ (1.013 g, 26.7 mmol), $LiAlD_4$ (1.120 g, 26.7 mmol) and THF (100 mL). The resultant suspension was stirred for 30 minutes before Stage 1 (6 g, 29.666 mmol) was charged portion-wise over 15 minutes at 20-40° C. The reaction mixture was then heated to reflux (66° C.) for 2 hours where HPLC indicated no Stage 1 remained. The mixture was cooled to 0° C. and quenched with 25% Rochelle's salts (aq) (120 mL) over 30 minutes at <30° C. The resultant milky suspension was stirred for 1 hour and then allowed to separate. The lower aqueous layer was removed and the upper organic layer washed with saturated brine (30 mL). The organics were then dried over $MgSO_4$, filtered and concentrated in vacuo. This provided 4.3 g of crude material. The crude was then taken up in ethanol (52 mL) and charged with fumaric acid (2.66 g, 22.917 mmol) before heating to 75° C. The resultant solution was allowed to cool to ambient temperature overnight before further cooling to 0-5° C. for 1 hour. The solids were isolated by filtration and washed with cold ethanol (6.5 mL×2). The filtercake was dried at 50° C. overnight to provided 5.7 g (yield=63%) of product in a purity of 99.9% by HPLC and >95% by NMR.

TABLE 1

| No. (LiAlH$_4$:LiAlD$_4$) | Input | Output (yield) | Purity HPLC | Purity by NMR | Deuteration % $D_0$ | $D_1$ | $D_2$ |
|---|---|---|---|---|---|---|---|
| SPL028i (0:1) | 5 g | 5.3 g (65%) | 99.7% | >95% | 0.7% | 2.7% | 96.6% |
| SPL028ii (1:1) | 6 g | 5.699 g (63%) | 99.9% | >95% | 30.0% | 48.3% | 21.7% |
| SPL028iii (1:2) | 5 g | 4.206 g (52%) | 99.9% | >95% | 16.5% | 46.8% | 36.8% |
| SPL028iv (1:3) | 5 g | 5.558 g (68%) | 99.8% | >95% | 9.3% | 41.5% | 49.2% |
| PSL028v (2:1) | 5 g | 4.218 g (52%) | 99.9% | >95% | 47.5% | 41.3% | 11.2% |
| SPL028vi (3:1) | 5 g | 5.0 g (62%) | 99.4% | >95% | 57.5% | 35.3% | 7.4% |

In Vitro Intrinsic Clearance of Deuterated DMT Compounds and Compositions

Human Hepatocyte Intrinsic Clearance

In vitro determination of intrinsic clearance (CLint) is a valuable model for predicting in vivo clearance. The liver contains both phase I and phase II drug metabolising enzymes, which are present in the intact cell and thereby provides a valuable model for the study of drug metabolism. In particular CLint in hepatocytes is a measure of the potential of a compound to undergo metabolism and can be related to hepatic clearance in vivo by also taking into consideration plasma protein binding and liver blood flow. Therefore, CLint may be used as an index of the relative metabolic stability of compounds and compared with other external probe substrates. Furthermore, the measurement of CLint in vitro, where hepatic metabolic clearance is known to be an issue, may be a useful means of understanding the different pharmacokinetic behaviour of compounds in vivo.

Assay Method

Human (mixed gender) hepatocytes pooled from 10 donors were used to investigate the in vitro intrinsic clearance of SPL026 and SL028 analogues in three separate experiments:

First experiment—Human (Mixed Gender) Hepatocytes; 0.545 million cells/mL. Final organic concentration 1.05% consisting of 80.74% of MeCN and 19.26% DMSO Second experiment—Human (Mixed Gender) Hepatocytes; 0.427 million cells/mL. Final organic concentration 1% consisting of 84.7% of MeCN and 15.3% DMSO.

Third experiment—Human (Mixed Gender) Hepatocytes; 0.362 million cells/mL

Mouse CD-1 (Male) Hepatocytes

Final organic concentration 1% consisting of 84.7% of MeCN and 15.3% DMSO

Assay Preparation

Hepatocyte buffer is prepared as 26.2 mM $NaHCO_3$, 9 mM Na HEPES, 2.2 mM D-Fructose and DMEM in MilliQ water.

Compound and marker stocks are prepared at 10 mM in DMSO and further diluted to 100× the assay concentration in 91:9 acetonitrile:DMSO.

Hepatocytes are thawed rapidly in a water bath at 37° C. and, once just thawed, decanted into hepatocyte buffer. Cells are centrifuged and the supernatant removed before counting and resuspension at the final assay concentration.

Assay Procedure

A concentration of 5 μM was used for all test compounds, as well as sumatriptan, serotonin, benzylamine controls with 2 replicate incubations per compound in each experiment. This concentration was chosen in order to maximise the signal-to-noise ratio, while remaining under the Michaelis constant ($K_m$) for the monoamine oxidase enzyme (MAO). Diltiazem and diclofenac controls were used at a laboratory-validated concentration of 1 μM.

Hepatocytes are added to pre-warmed incubation tubes (37° C.). Pre-prepared 100× assay compound stocks are then added to the incubation tubes and mixed carefully. Samples are taken at 7 time points (2, 4, 8, 15, 30, 45 and 60 minutes). At each timepoint, small aliquots were withdrawn from the incubation and quenched 1:4 with ice-cold acidified methanol or acetonitrile containing internal standard.

Incubation tubes are orbitally shaken at 37° C. throughout the experiment.

Standard final incubation conditions are 1 μM compound in buffer containing nominally ~0.5 million viable cells/mL, ~0.9% (v/v) acetonitrile (MeCN) and ~0.1% (v/v) DMSO (specific assay concentrations outlined above, section 2).

Quenched samples are mixed thoroughly, and protein precipitated at –20° C. for a minimum of 12 hours. Samples are then centrifuged at 4 oc. Supernatants are transferred to a fresh 96-well plate for analysis.

Liquid Chromatography-Mass Spectrometry (LC-MS/MS)

The following LC-MS/MS conditions were used for the analysis:

Instrument: Thermo TSQ Quantiva with Thermo Vanquish UPLC system
Column: Luna Omega 2.1×50 mm 2.6 μm
Solvent A: $H_2O$+0.1% formic acid
Solvent B: Acetonitrile+0.1% formic acid
Flow rate: 0.8 ml/min
Injection vol: 1 μl
Column temp: 65° C.
Gradient (see TABLE 2):

TABLE 2

| Time (mins) | % Solvent B |
|---|---|
| 0.00 | 5.0 |
| 0.90 | 75.0 |
| 1.36 | 99.0 |
| 1.36 | 5.0 |
| 1.80 | 5.0 |

MS parameters:
Positive ion spray voltage: 4000 V
Vaporiser temperature: 450° C.
Ion transfer tube temp: 365° C.
Sheath gas: 54
Aux gas: 17
Sweep gas: 1
Dwell time 8 ms MRM transitions:
D0=mass to charge ratio 189.136>144.179 (method determined from SPL026 analysis)
D1=mass to charge ratio 190.136>59.17 (method determined from SPL028ii analysis)
D2=mass to charge ratio 191.137>60.169 (method determined from SPL028i analysis)
D6=mass to charge ratio 195.17>64.127
D8=mass to charge ratio 197.2>146.17

The MRM transitions were determined from a preliminary analysis of DMT samples containing either no deuterium (for D0 transition), or high levels of either D1, D2, D6 or D8 deuteration (for the D1, D2, D6 and D8 transitions respectively).

The resulting concentration-time profile was then used to calculate intrinsic clearance (CLint) and half-life (t½%). To do this, the MS peak area or MS peak area/IS response of each analyte is plotted on a natural log scale on the y axis versus time (min) of sampling on the X axis. The slope of this line is the elimination rate constant. This is converted to a half-life by –ln(2)/slope. Intrinsic clearance is calculated from the slope/elimination rate constant and the formula is CLint=(–1000*slope)/cell denisty in 1E6 cells/ml, to give units of microlitre/min/million cells.

Clearance of Six Different $D_2DMT$ Analogue Blends (SPL028i-SPL0280 with and without MAO Inhibitors The contribution of MAO of six different α,α,-dideutero-N,N-dimethyltryptamine ($D_2DMT$) compounds was examined using an irreversible, combined MAO-NB inhibitor (100 nM clorgyline and 100 nM Deprenyl/Selegiline added as a cassette) via the measurement of in vitro intrinsic clearance using human (mixed gender) hepatocytes from 10 donors (0.545 million cell s/mL; final organic concentration 1.05% consisting of 80.74% of MeCN and 19.26% DMSO).

Effect of Deuteration

Data were fitted with two separate linear models using linear regression analyses (one-way ANOVA), which revealed that deuterium enrichment at the α-carbon of DMT decreases intrinsic clearance linearly with increasing percentage of $D_2$-deuteration using the Formula: y=$D_2$*–6.04+ 12.9, $r^2$=0.748 and molecular weight (MW) using the Formula: y=MW*79.5+98.8, $r^2$=0.811.

96.6% $D_2$-DMT (SPL028i) saw the biggest change in metabolic stability, ~2-fold change in intrinsic clearance and half-life compared to SPL026 in initial hepatocyte studies (TABLE 3 and TABLE 4). The metabolic stability of intermediate blends of deuteration (SPL028ii-SPL028vi) increased in a manner which correlated with increasing level of deuteration and molecular weight (TABLE 3 and TABLE 4).

TABLE 3 shows in vitro Intrinsic clearance of SPL026 and 6 different $D_2$-deuterated SPL028 analogue blends in in human hepatocytes, highlighting the fold change in intrinsic clearance from SPL026 for each deuterated compound, with and without inhibitors. Compounds ordered via molecular weight.

TABLE 3

| Cpd name | Molecular weight | Ratio of deuteration ($D_0$:$D_1$:$D_2$) | Intrinsic clearance (μL/min/million cells) Without inhibitors | Fold change from SPL026 | With inhibitors | Fold change from SPL026 |
|---|---|---|---|---|---|---|
| SPL026 | 188.27 | 100:0:0 | 13.77 | 1.00 | 13.24 | 1.00 |
| SPL028v | 188.9098 | 48:41:11 | 10.99 | 1.25 | 9.51 | 1.39 |

TABLE 3-continued

| Cpd name | Molecular weight | Ratio of deuteration ($D_0:D_1:D_2$) | Intrinsic clearance (µL/min/million cells) | | | |
|---|---|---|---|---|---|---|
| | | | Without inhibitors | Fold change from SPL026 | With inhibitors | Fold change from SPL026 |
| SPL028vi | 188.9613 | 57:35:7 | 13.64 | 1.01 | 10.79 | 1.23 |
| SPL028ii | 189.1915 | 30:48:22 | 10.46 | 1.32 | 8.78 | 1.51 |
| SPL028iii | 189.6685 | 17:47:37 | 9.36 | 1.47 | 6.90 | 1.92 |
| SPL028iv | 189.6764 | 9:42:49 | 11.14 | 1.24 | 7.46 | 1.77 |
| SPL028i | 190.2398 | 1:3:97 | 7.15 | 1.93 | 7.50 | 1.77 |
| Benzylamine | | | 16.70 | | <3.0 | |
| Serotonin | | | 38.60 | | 10.10 | |

TABLE 4 shows in vitro half-life of SPL026 and 6 different $D_2$-deuterated SPL028 analogue blends in in human hepatocytes, highlighting the fold change in intrinsic clearance from SPL026 for each deuterated compound, with and without inhibitors. Compounds ordered via molecular weight.

TABLE 4

| Cpd name | Molecular weight | Ratio of deuteration ($D_0:D_1:D_2$) | Without inhibitors | Fold change from SPL026 | With inhibitors | Fold change from SPL026 |
|---|---|---|---|---|---|---|
| SPL026 | 188.27 | 100:0:0 | 92.39 | 1.00 | 96.06 | 1.00 |
| SPL028v | 188.9098 | 48:41:11 | 119.61 | 1.29 | 135.10 | 1.41 |
| SPL028vi | 188.9613 | 57:35:7 | 95.04 | 1.03 | 119.62 | 1.25 |
| SPL028ii | 189.1915 | 30:48:22 | 125.80 | 1.36 | 147.47 | 1.54 |
| SPL028iii | 189.6685 | 17:47:37 | 140.43 | 1.52 | 189.60 | 1.97 |
| SPL028iv | 189.6764 | 9:42:49 | 116.84 | 1.26 | 171.17 | 1.78 |
| SPL028i | 190.2398 | 1:3:97 | 178.79 | 1.94 | 169.75 | 1.77 |
| Benzylamine | | | 76.30 | | 460.00 | |
| Serotonin | | | 33.00 | | 125.70 | |

Figure 4:
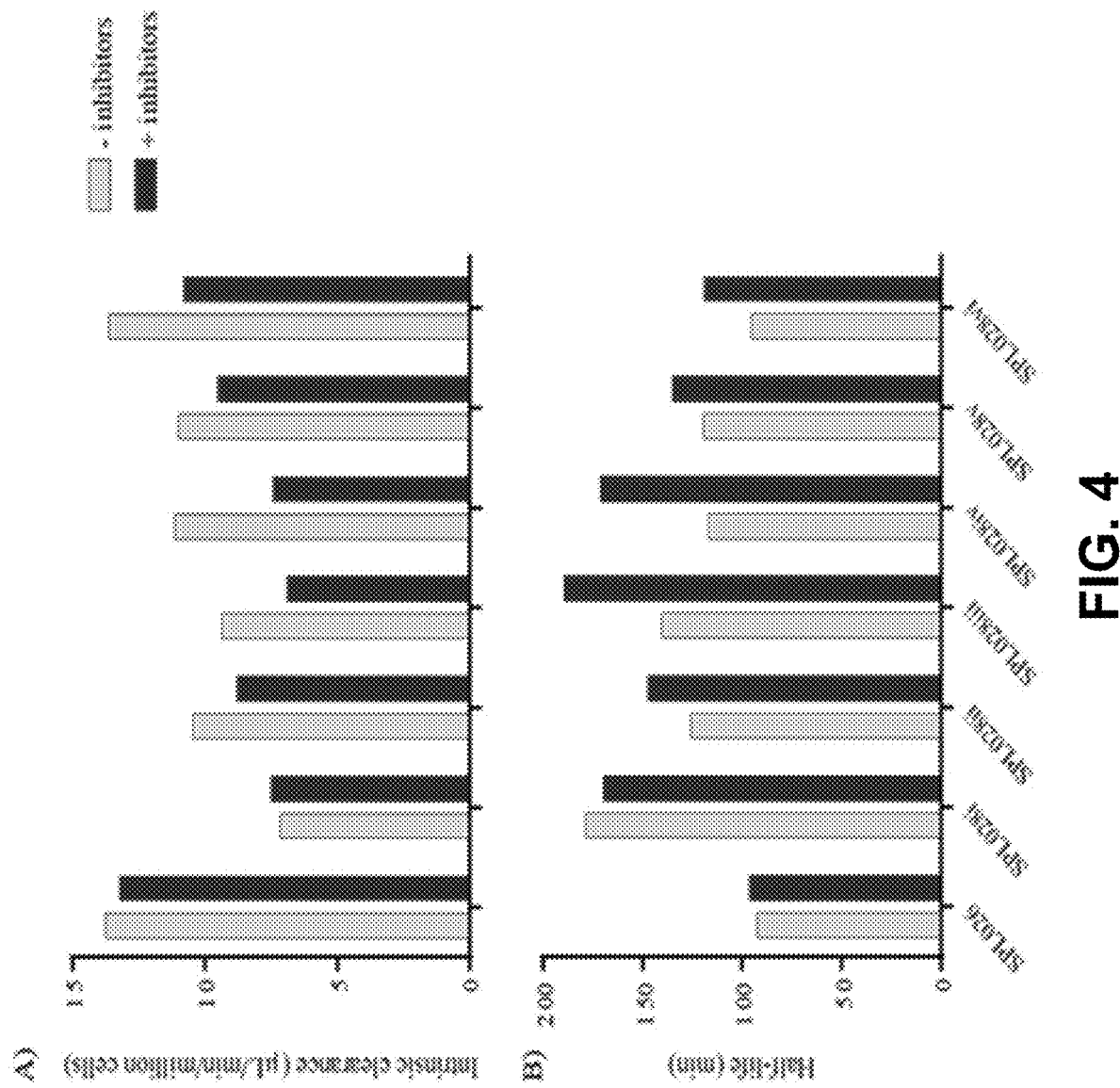
FIG. 4 In vitro intrinsic clearance (A) and half-life (B) of DMT (SPL026) and 6 different $D_2$-deuterated SPL028 analogue blends in human hepatocytes with and without MAO-A/B inhibitor combination, as described in the Example section, below.

Contribution of MAO (See Also FIG. 4)

Two-way ANOVA was carried out to determine the influence of MAO inhibitors and compound deuteration on intrinsic clearance. There was a significant effect of MAO inhibitors on intrinsic clearance $F(1, 6)=11.42$, $p=0.0149$, and deuteration on intrinsic clearance $F(1,6)=9.996$, $p=0.006$.

The inclusion of MAO inhibitors was shown to have minimal effect on the metabolism of SPL026 (DMT) resulting in ~4% slower intrinsic clearance (TABLE 5). MAO inhibitors were also shown to have a small effect on the 96.6% $D_2$-deuterated analgoue (SPL028i) which saw a ~5% quicker intrinsic clearance in the presence of MAO inhibitors (TABLE 5). These results indicate that MAO enzymes do not significantly contribute to the metabolism of SPL026 and SPL028i in human liver hepatocytes.

MAO inhibitors were shown to have a greater inhibitory effect on intrinsic clearance for the remaining five $D_2$-deuterated analogue blends (SPL028ii-SPL028vi). For these five compounds, the inhibitory action of MAO inhibitors was shown to increase linearly with increasing level of deuteration and molecular weight, with the exception of SPL028vi (TABLE 3). 49% $D_2$-deuterated SPL028iv saw the largest change in intrinsic clearance (49%) with the inclusion of MAO inhibitors (TABLE 5), whereas 36.8% $D_2$-deuterated SPL028iii saw the largest change (~2 fold) in metabolic stability relative to SPL026 in cellular fractions with inhibitors (TABLE 3 and 4).TABLE 5 In vitro Intrinsic clearance and half-life of SPL026 and 6 different D2-deuterated SPL028 analogue blends in in human hepatocytes with and without MAO-A/B inhibitor combination. Percentage change (%) values represent the % change in metabolic stability with the inclusion of MAO inhibitors vs no inhibitors, measured by intrinsic clearance and half-life separately. Compounds are ordered by increasing molecular weight.

TABLE 5

| Cpd Name | Mol. weight | Ratio of deuteration ($D_0:D_1:D_2$) | Intrinsic clearance (µL/min/million cells) | | | Half-life (min) | | |
|---|---|---|---|---|---|---|---|---|
| | | | Without inhibitors | With inhibitors | % change | Without inhibitors | With inhibitors | % change |
| SPL026 | 188.27 | 100:0:0 | 13.77 | 13.24 | -4.00 | 92.39 | 96.06 | 3.82 |
| SPL028v | 188.9098 | 48:41:11 | 10.99 | 9.51 | -15.56 | 119.61 | 135.1 | 11.47 |
| SPL028vi | 188.9613 | 57:35:7 | 13.64 | 10.79 | -26.41 | 95.04 | 119.62 | 20.55 |
| SPL028ii | 189.1915 | 30:48:22 | 10.46 | 8.78 | -19.13 | 125.8 | 147.47 | 14.69 |
| SPL028iii | 189.6685 | 17:47:37 | 9.36 | 6.9 | -35.65 | 140.43 | 189.6 | 25.93 |
| SPL028iv | 189.6764 | 9:42:49 | 11.14 | 7.46 | -49.33 | 116.84 | 171.17 | 31.74 |
| SPL028i | 190.2398 | 1:3:97 | 7.15 | 7.5 | 4.67 | 178.79 | 169.75 | -5.33 |

TABLE 5-continued

| Cpd Name | Mol. weight | Ratio of deuteration ($D_0$:$D_1$:$D_2$) | Intrinsic clearance (μL/min/million cells) | | | Half-life (min) | | |
|---|---|---|---|---|---|---|---|---|
| | | | Without inhibitors | With inhibitors | % change | Without inhibitors | With inhibitors | % change |
| Benzylamine | | | 16.7 | <3.0 | <−450 | 76.3 | 460 | >83.41 |
| Serotonin | | | 38.6 | 10.1 | −282.18 | 33 | 125.7 | 73.75 |

These results indicate that increasing the level of deuteration at the α-carbon of DMT decreases the MAO enzyme metabolism of the compound.

Clearance of Six $D_2$DMT Analogue Blends (SPL028i-SPL028vi) and One $D_6$-DMT (SPL028vii) Analogue Blends
Synthesis of d6-DMT: 028vii (Compound 5)
Stage 1

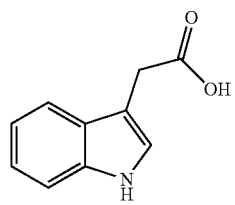

Molecular Weight: 175.18

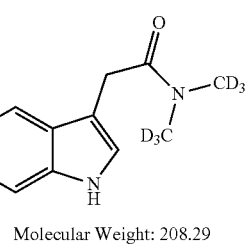

Molecular Weight: 208.29

EDC.HCl (15.7 g, 81.90 mmol) was added to 3-indoleacetic acid (12.0 g, 68.50 mmol) and HOBt.H2O (1.16 g, 75.75 mmol) in DCM (108 mL) at room temperature. The reaction was stirred for 1 hour after which N,N-diisopropylethylamine (DIPEA) (35.6 mL, 205.75 mmol) and d6-dimethylamine.HCl (9.0 g, 102.76 mmol) were added (temperature maintained below 30° C.). The reaction was stirred for 1 hour at room temperature after which analysis by HPLC indicated 65.6% product with 28.9% 3-indoleacetic acid remaining. DIPEA (11.9 mL, 68.78 mmol) was added and the reaction was stirred for 1 hour at room temperature. HPLC indicated no change in conversion. Aqueous potassium carbonate (6.0 g in 54 mL water) was added and the phases were separated. The aqueous phase was extracted with DCM (2×30 mL). The combined organics were washed with brine (2×30 mL) then aqueous citric acid (20 w/w %, 50 mL), dried over MgSO4 and filtered. The filtrate was stripped and the resulting solids were slurried in TBME (120 mL) and isolated by filtration. Purification by flash column chromatography yielded 8.34 g of the desired product (58% yield). $^1$H NMR confirmed the identity of the product.

Stage 2

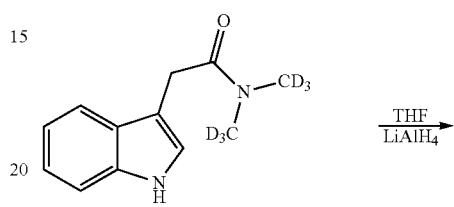

Molecular Weight: 208.29

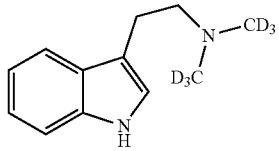

Molecular Weight: 194.31

LiAlH4 (1 M in THF, 17.3 mL, 17.28 mmol) was added to a suspension of Stage 1 (4.0 g, 19.20 mmol) in THF (10 mL) at <30° C. The resulting reaction was heated to 60-65° C. and stirred for 2 hours. HPLC analysis indicated complete consumption of Stage 1 with 97.3% product formed. The reaction was cooled to room temperature and quenched into aqueous Rochelle's salts (10 g in 30 mL water) at <30° C. After stirring for 1 hour, the phases were separated. The aqueous phase was extracted with THF (20 mL). The combined organics were washed with brine (20 mL), dried over MgSO4, filtered and stripped (azeotroped with ethanol, 20 mL) to give the desired product as an amber oil (3.97 g). $^1$H NMR confirmed the identity of the product and indicated 8.5% ethanol was present (no THF) giving an active yield of 3.63 g, 97%.

Stage 3

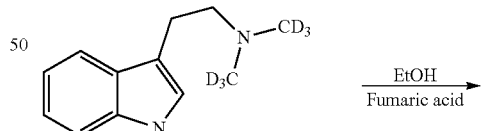

Molecular Weight: 194.31

Molecular Weight: 310.38 d6-DMT free base (3.6 g active, 18.53 mmol) was dissolved in ethanol (43 mL) at room temperature. Fumaric acid (2.15 g, 18.53 mmol) was added and the solution was heated to 75° C. (solids crystallised during heating and did not re-dissolve). The resulting suspension was cooled to 0-5° C. and stirred for 1 hour. The solids were isolated by filtration, washed with ethanol (2×7 mL) and pulled dry. Further drying in a vacuum oven at 50° C. yielded the desired d₆-DMT fumaric acid salt (4.98 g, 87%).

Synthesis of d₆-DMT: 028viii (Compound 1)

For Stage 1 (coupling of 3-indoleacetic acid and d₆-dimethylamine), see above

Stage 2

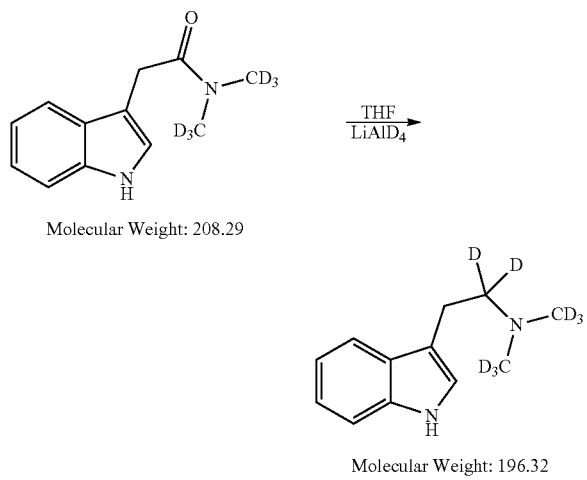

Molecular Weight: 208.29

Molecular Weight: 196.32

LiAlD₄ (1 M in THF, 17.3 mL, 17.28 mmol) was added to a suspension of Stage 1 (4.0 g, 19.20 mmol) in THF (10 mL) at <30° C. The resulting reaction was heated to 60-65° C. and stirred for 2 hours. HPLC analysis indicated complete consumption of the Stage 1 with 97.3% product formed. The reaction was cooled to room temperature and quenched into aqueous Rochelle's salts (10 g in 30 mL water) at <30° C. After stirring for 1 hour, the phases were separated. The aqueous phase was extracted with THF (20 mL). The combined organics were washed with brine (20 mL), dried over MgSO₄, filtered and stripped (azeotroped with ethanol, 20 mL) to give the desired product as an amber oil (4.01 g).

¹H NMR confirmed the identity of the product and indicated 8.6% ethanol was present (no THF) giving an active yield of 3.66 g, 97%.

Stage 3

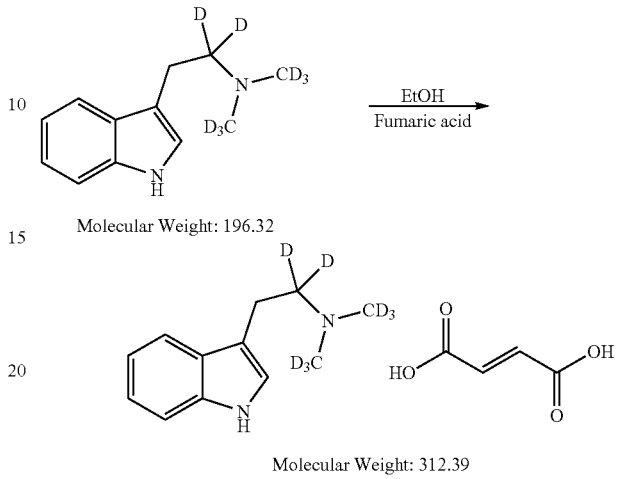

Molecular Weight: 196.32

Molecular Weight: 312.39

Compound 1 free base (3.6 g active, 18.53 mmol) was dissolved in ethanol (43 mL) at room temperature. Fumaric acid (2.15 g, 18.53 mmol) was added and the solution was heated to 75° C. (solids crystallised during heating and did not re-dissolve). The resulting suspension was cooled to 0-5° C. and stirred for 1 hour. The solids were isolated by filtration, washed with ethanol (2×7 mL) and pulled dry. Further drying in a vacuum oven at 50° C. yielded the desired Compound 1 as a fumaric acid salt (4.62 g, 81%).

Assessment of Extents of Deuteration

This was achieved by LCMS-SIM (SIM=single ion monitoring), the analysis giving a separate ion count for each mass for the three deuterated N,N-dimethyltryptamine compounds (N,N-dimethyltryptamine (D0), α-protio, α-deutero-N,N-dimethyltryptamine (D1) and α,α-dideutero-N,N-dimethyltryptamine (D2)) at the retention time for N,N-dimethyltryptamine. The percentage of each component was then calculated from these ion counts.

For example, % D0=[D0/(D0+D1+D2)]×100.

| HPLC Parameters | | | | |
|---|---|---|---|---|
| System: | Agilent 1100/1200 series liquid chromatograph or equivalent | | | |
| Column: TPH12S03-1546PTH) | Triart Phenyl; 150 × 4.6 mm, 3.0 μm particle size (Ex: YMC, Part number: | | | |
| Mobile phase A: | Water: Trifluoroacetic acid (100:0.05%) | | | |
| Mobile phase B: | Acetonitrile : Trifluoroacetic acid (100:0.05%) | | | |
| Gradient: | Time | % A | | % B |
| | 0 | 95 | | 5 |
| | 13 | 62 | | 38 |
| | 26 | 5 | | 95 |
| | 30.5 | 5 | | 95 |
| | 31 | 95 | | 5 |
| Flow rate: | 1.0 mL/min | | | |
| Stop time: | 31 minutes | | Post runtime: | 4 minutes |
| Injection volume: | 5 μL | | Wash vial: | N/A |
| Column temperature: | 30° C. combined | | | |
| Wavelength: | 200 nm, (4 nm) Reference: | | N/A | |

-continued

Mass spectrometry parameters

| System: | Agilent 6100 series Quadrupole LC-MS or equivalent | | |
|---|---|---|---|
| Drying gas flow: | 12.0 L/min | Drying gas temp.: | 350° C. |
| Nebuliser pressure: | 35 psig | | |
| Fragmentor: | 110 | Gain: | 1.00 |

| Cpd | RT | RRT | Conc | Diluent | Detection Mass |
|---|---|---|---|---|---|
| D0 | 10.64 | 1.00 | 0.30 mg/ml | $CH_3CN:H_2O$ (50:50) | (+) SIM 189.10 m/z |
| D1 | 10.64 | 1.00 | 0.30 mg/ml | $CH_3CN:H_2O$ (50:50) | (+) SIM 190.10 m/z |
| D2 | 10.64 | 1.00 | 0.30 mg/ml | $CH_3CN:H_2O$ (50:50) | (+) SIM 191.10 m/z |

MS-SIM range is the target mass ± 0.1 m/z

In vitro human hepatic intrinsic clearance of the six different α,α,-dideutero-N,N-dimethyltryptamine ($D_2$DMT) compounds and one N,N-bis(trideutero-dimethyl)tryptamine ($D_6$DMT, SPL028vii) were measured to investigate the effects of methyl group deuteration vs α-carbon deuteration on metabolic stability in using human (mixed gender) hepatocytes from 10 donors (0.427 million cells/mL; final organic concentration 1% consisting of 84.7% of MeCN and 15.3% DMSO). TABLE 6 shows in vitro intrinsic clearance and half-life of 6 different $D_2$-deuterated DMT and $D_6$-deuterated DMT analogue blends in human hepatocytes, ordered by increasing level of molecular weight.

TABLE 6

| Compound Name | Intrinsic clearance (μL/min/million cells) | Half-life (min) |
|---|---|---|
| SPL028v | 14.1 | 119 |
| SPL028vi | 13.4 | 126.8 |
| SPL028ii | 9.1 | 191.1 |
| SPL028iii | 8.2 | 213.9 |
| SPL028iv | 7.7 | 223.9 |
| SPL028i | 6.3 | 258.3 |
| SPL028vii ($D_6$) | 13.3 | 122.2 |
| Diltiazem (A) | 15.3 | 15.0 |
| Diltiazem (B) | 17.2 | 18.2 |
| Diclofenac (A) | 155.0 | 154.0 |
| Diclofenac (B) | 150.1 | 154.3 |

Data fitted with a linear regression model on the six different $D_2$-deuterated confirmed previous findings that deuterium enrichment at the α-carbon of DMT decreases intrinsic clearance linearly with increasing level of $D_2$-deuteration, $y=D_2*-8.07+12.9$, $r^2=0.690$ and molecular weight. A linear regression model was also fitted by molecular weight using Formula: $y=MW*13.9+6.06$, $r^2=0.923$ revealing molecular weight is a strong predictor of intrinsic clearance for the 6 different $D_2$-deuterated SPL028 blends.

Initial hepatocyte data did not suggest a relationship between molecular weight and intrinsic clearance of $D_2$-deuterated and $D_6$-deuterated SPL028 blends, $r^2=0.0395$.

Example 2

In the second example, the inventors detect a possible increase in half-life when N,N-dimethyltryptamine is deuterated at the N,N-dimethyl position.

Clearance of Two $D_2$DMT (SPL028i and SPL028ii Blends, One $D_6$DMT (SPL028vii, Compound 5) and One $D_8$-DMT (SPL028viii, Compound 1) Analogue Further human hepatocyte assays were conducted with two $D_2$-deuterated SLP028 analogue blends and two additional deuterated analogues: $D_6$DMT and $D_8$DMT to measure in vitro intrinsic clearance using human (mixed gender) hepatocytes from 10 donors (0.362 million cells/mL). TABLE 7 shows in vitro intrinsic clearance and half-life of two different $D_2$-deuterated DMT, $D_6$-deuterated DMT and $D_8$-deuterated DMT analogue blends in human hepatocytes, ordered by increasing level of molecular weight.

TABLE 7

| Compound Name | Intrinsic Clearance (μL/min/ million cells) | Fold change from SPL026 | Half-life (min) | Fold change from SPL026 |
|---|---|---|---|---|
| SPL026 | 19.4 | 1.0 | 98.9 | 1.0 |
| SPL028ii | 11.7 | 1.7 | 170.9 | 1.7 |
| SPL028i | 8.3 | 2.3 | 233.1 | 2.4 |
| SPL028vii (Compound 5) | 17.1 | 1.1 | 112.1 | 1.1 |
| SPL028viii (Compound 1) | 9.3 | 2.1 | 206.9 | 2.1 |
| Diltiazem | 22.0 | | 87.3 | |
| Diclofenac | 92.5 | | 20.7 | |

The possible presence of a secondary kinetic isotope effect was noted in the data, however a linear regression model did not support a predictive relationship between molecular weight and intrinsic clearance for SPL026, SPL028i, SPL028ii, SPL029vii and SPL028viii, $r^2=0.0445$ in the human hepatocyte assay.

Example 3

In the third example, the inventors provide evidence that an additional protective effect is observed between $D_2$-deuterated SPL028i and $D_8$-deuterated SPL028viii (Compound 1). The data are supportive of a synergistic effect on metabolic stability when deuterium is present at both the alpha position and the N,N-dimethyl positions of a compound of Formula I or any other compound or composition of any aspect described herein.

Use of Liver Mitochondrial Fraction to Model Human Metabolism of Deuterated DMT

Given the predicted 5 minute half-life of DMT in humans, the inventors expect that DMT is largely broken down before reaching the human liver. Therefore, a non-tissue or organ specific alternative in vitro assay was sought as a more appropriate system to model human metabolism of DMT. An analysis of non-tissue or organ specific human metabolism may be carried out in Human Liver Mitochondrial Fractions.

The following assays conducted on Human Liver Mitochondrial (HLMt) fractions predict enhanced fold-change between SPL026 and $D_2$-deuterated SPL028i compared with the fold-change predicted in hepatocyte studies.

In Vitro Human Mitochondrial Fraction Intrinsic Clearance of SPL026 (DMT) with/without MAO-A and MAO-B Inhibitors In vitro determination of the intrinsic clearance of SPL026 with selective and irreversible MAO-A inhibitor (100 nM clorgyline) and MAO-B inhibitor (100 nM Deprenyl/Selegiline) were added separately to 0.5 mg/mL of human liver mitochondrial fraction. The MAO-A substrate, Serotonin and MAO-B substrate, Benzylamine were added as positive controls which confirmed the presence of MAO-A and MAO-B and the action of Clorgyline and Deprenyl inhibitors. TABLE 8 shows intrinsic clearance and half-life of SPL026 in human liver mitochondrial fraction.

TABLE 8

| Compound Name | Inhibitor | Intrinsic Clearance (µL/min/mg protein) | Half-life (min) |
|---|---|---|---|
| SPL026 | DMSO Vehicle | 42.9 | 33.7 |
| SPL026 | Clorgyline (MAO-A inhibitor) | <3.9 | >373.7 |
| SPL026 | Deprenyl (MAO-B inhibitor) | 42.7 | 32.5 |
| Serotonin | DMSO Vehicle | 124.6 | 11.1 |
| Serotonin | Clorgyline | <3.3 | >420.2 |
| Benzylamine | DMSO Vehicle | 45.7 | 30.4 |
| Benzylamine | Deprenyl | <3.3 | >420.2 |

SPL026 half-life and intrinsic clearance significantly increased with MAO-A inhibitor (Clorgyline), resulting in a 10-fold increase in intrinsic clearance compared data from SPL026 without MAO inhibitors. Deprenyl (MAO-B inhibitor) showed no difference in human mitochondrial intrinsic clearance relative to fraction without inhibitors. These results suggest that a role of MAO-A but not MAO-B, in the metabolism of SPL026.

In Vitro Human Mitochondrial Fraction Intrinsic Clearance of SPL026 (DMT), SPL028i (96.6% $D_2$-DMT), SPL028iii (36.8% $D_2$-DMT), SPL028vii (Compound 5) and SPL028viii (Compound 1)

In vitro determination of the intrinsic clearance of SPL026, SPL028i, SPL028iii and SPL028viii were added separately to 0.5 mg/mL of human liver mitochondrial fraction. The MAO-A substrate 'Serotonin' and MAO-B substrate 'Benzylamine' were added as positive controls and confirmed the presence of MAO-A and MAO-B. The experiment was repeated with the same substances and also with SPL028iii and SPL028vii. TABLE 9 shows intrinsic clearance and half-life of SPL026, SPL028i, SPL028ii, SPL028iii, SPL028vii and SPL028viii in human liver mitochondrial fraction.

TABLE 9

| Compound Name | Intrinsic Clearance (µL/min/ mg protein) | 1/Fold change from SPL026 | Half-life (min) | Fold change from SPL026 |
|---|---|---|---|---|
| SPL026 | 161.0 | 1.0 | 8.6 | 1.0 |
| SPL028iii | 15.0 | 3.6 | 31.1 | 3.6 |
| SPL028i | 44.6 | 10.7 | 92.8 | 10.8 |
| SPL028viii | 10.9 | 14.8 | 127.7 | 14.8 |
| Serotonin | 151.0 | — | 9.2 | — |
| Benzylamine | 60.0 | — | 23.2 | — |
| SPL026 | 175.0 | 1.0 | 7.9 | 1.0 |
| SPL028vii | 137.1 | 1.3 | 10.2 | 1.3 |
| SPL028ii | 47.3 | 3.7 | 29.4 | 3.7 |
| SPL028iii | 39.8 | 4.4 | 34.8 | 4.4 |
| SPL028i | 18.0 | 9.7 | 77.3 | 9.7 |
| SPL028viii | 12.7 | 13.7 | 112.2 | 14.1 |
| Serotonin | 157.0 | — | 22.4 | — |
| Benzylamine | 62.1 | — | 8.8 | — |

Half-life increased with increasing level of deuteration for the SPL028 compounds, when compared to SPL026. D8-deuterated SPL028viii (Compound 1) saw the greatest change in half-life (14 fold increase when averaged across both repeats) relative to SPL026. 96.6% $D_2$-deuterated SPL028i also showed a large change in half-life (10 fold increase when averaged across both repeats) compared to SPL026. 36.80% $D_2$-deuterated SPL028iii demonstrated a smaller change (3.6 fold increase) in clearance compared to SPL026. An independent Welch's t-test was performed for each deuterated compound compared to SPL026, results are provided in TABLE 10 t-test showing significance of half-life extension of SPL028(i-viii).

TABLE 10

| Compound Name | Half-Life (min) | | | | t-test vs SPL026) |
| | R1 | R2 | R3 | R4 | p value |
|---|---|---|---|---|---|
| SPL026 | 8.8 | 8.4 | 7.6 | 8.3 | |
| SPL028i | 86.1 | 99.4 | 82.6 | 72.1 | 0.0004297 |
| SPL028ii | | | 28.0 | 30.7 | 0.0206256 |
| SPL028iii | 31.5 | 30.7 | 34.7 | 35.0 | 0.0001036 |
| SPL028vii | | | 9.4 | 10.9 | 0.1211645 |
| SPL028viii | 121.4 | 133.9 | 92.9 | 131.5 | 0.0006452 |
| Benzylamine | 24.3 | 22.1 | 21.2 | 23.5 | |
| Serotonin | 9.3 | 9.1 | 9.1 | 8.5 | |

Complete deuteration at the alpha position of N,N-dimethyltryptamine increases metabolic stability 10-fold via primary kinetic isotope effect in human mitochondrial fraction assays.

N,N-dimethyl deuteration potentially increases metabolic stability via secondary kinetic isotope effect in human hepatocyte assays.

Most unexpectedly, the primary and secondary isotope effects of deuteration at both the alpha position and the N,N-dimethyl position increase metabolic stability synergistically in Compound 1, demonstrated with a 14-fold increase metabolic stability in human mitochondrial fraction assays.

The invention claimed is:
1. A therapeutic composition comprising:
   a deuterated N,N-dimethyltryptamine compound of Formula (I) or a pharmaceutically acceptable salt thereof:

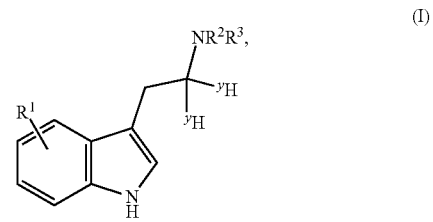

wherein:
each $R^1$ is H;
$R^2$ is $CD_3$;
$R^3$ is $CD_3$; and
each $^3H$ is independently selected from H and D.

2. The composition of claim 1, wherein the compound is in the form of a pharmaceutically acceptable salt, and wherein the pharmaceutically acceptable salt is a fumarate salt.

3. The composition of claim 1, wherein the composition is a pharmaceutical dosage form.

4. The composition of claim 3, wherein the pharmaceutical dosage form is a parenteral dosage form.

5. The composition of claim 3, wherein the pharmaceutical dosage form is a solid dosage form.

6. The composition of claim 3, wherein the pharmaceutical dosage form comprises from 0.001 mg to 100 mg of the deuterated N,N-dimethyltryptamine compound, or a pharmaceutically acceptable salt thereof.

7. The composition of claim 1, wherein the compound is Compound 1:

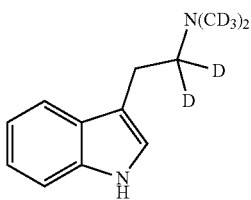

, or a pharmaceutically acceptable salt thereof.

8. The composition of claim 7, wherein the composition is a pharmaceutical dosage form.

9. The composition of claim 1, wherein the compound is Compound 2:

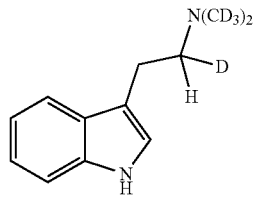

, or a pharmaceutically acceptable salt thereof.

10. The composition of claim 9, wherein the composition is a pharmaceutical dosage form.

11. The composition of claim 1, wherein the compound is Compound 5:

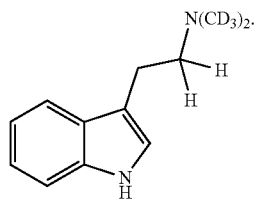

, or a pharmaceutically acceptable salt thereof.

12. The composition of claim 11, wherein the composition is a pharmaceutical dosage form.

* * * * *